United States Patent [19]
Zavracky et al.

[11] Patent Number: 5,528,397
[45] Date of Patent: Jun. 18, 1996

[54] SINGLE CRYSTAL SILICON TRANSISTORS FOR DISPLAY PANELS

[75] Inventors: Paul M. Zavracky, Norwood; John C. C. Fan, Chestnut Hill; Robert McClelland, Norwell, all of Mass.; Jeffrey Jacobsen, Hollister, Calif.; Brenda Dingle, Norton, Mass.

[73] Assignee: Kopin Corporation, Taunton, Mass.

[21] Appl. No.: 281,777

[22] Filed: Jul. 28, 1994

Related U.S. Application Data

[63] Continuation of Ser. No. 225,091, Apr. 8, 1994, Pat. No. 5,362,671, which is a continuation of Ser. No. 85,667, Jun. 30, 1993, abandoned, which is a continuation of Ser. No. 801,966, Dec. 3, 1991, abandoned, and a division of Ser. No. 636,602, Dec. 31, 1990, Pat. No. 5,206,749.

[51] Int. Cl.$^6$ .......................... H01L 27/01; G02F 1/136; G09C 3/10
[52] U.S. Cl. .......................... 359/59; 359/74; 315/169.3; 257/347; 257/353
[58] Field of Search .......................... 359/59, 74; 257/347, 257/352, 353; 315/169.3

[56] References Cited

U.S. PATENT DOCUMENTS

| | | | |
|---|---|---|---|
| 3,955,190 | 5/1976 | Teraishi | 345/32 |
| 4,024,626 | 5/1977 | Leupp et al. | 437/60 |
| 4,266,223 | 5/1981 | Frame | 345/80 |
| 4,270,846 | 6/1981 | Miyamoto | 359/89 |

(List continued on next page.)

FOREIGN PATENT DOCUMENTS

| | | | |
|---|---|---|---|
| 0151508 | 8/1985 | European Pat. Off. | |
| 0268380 | 5/1988 | European Pat. Off. | 359/59 |
| 57-106181 | 7/1982 | Japan . | |
| 63-55529 | 3/1988 | Japan | 359/59 |
| 63-10130 | 5/1988 | Japan | 359/59 |
| 63-101831 | 5/1988 | Japan | 359/59 |
| 64-38727 | 2/1989 | Japan . | |

OTHER PUBLICATIONS

Ipri, A. C. et al., "A 600°–650° C. Polysilicon CMOS Process for Fabricating Fully Scanned Active∝matrix LCDs," *Proceedings of the SID*, (29)2:167–171, (1988).

Milnes, A. G., "Semiconductor Heterojunciton Topics: Introduction and Overview," *Solid–State Electronics*, (20) 2:99–121 (1986).

Hamaguchi, et al., "Device Layer Transfer Technique using Chemo–mechanincal Polishing," *Japanese Journal of Applied Physics*, 923)10:L815–L817, (Oct. 1984).

Fujii, Eiji et al., "A Laser–Recrystallization Technique for Silicon–TFT Integrated Circuits on Quartz Substrates and Its Application to small–size Monolithic Active–matrix LCD's," *Transactions on Electron Devices*, (37):121–126, (Jan. 1990).

Sumiyoshi et al., "Device layer Tansferred Poly Si TFT Array For High Resolution Liquid Crystal Projector", *IEDM* (1989):165–168.

Takahashi et al., "Effects Of Adhesive Properties On SOI Devices Otained by Device Transfer Method", *IEEE* (1990):147–148.

Stix, "Manufacturing Hurdles Challenge Large–LCD Developers", *IEEE Spectrum, Special Report* 91989):36–40.

Turner et al., "High–speed Photoconductive Detectors Fabricated in Heteroepitaxial GaAs Layers", *Mat. Res. Sec. Symp. Proc.* vol. 67 (1986):181–188.

(List continued on next page.)

*Primary Examiner*—William L. Sikes
*Assistant Examiner*—Ron Trice
*Attorney, Agent, or Firm*—Hamilton, Brook, Smith & Reynolds

[57] ABSTRACT

A display panel is formed using essentially single crystal thin-film material that is transferred to substrates for display fabrication. Pixel arrays form light valves or switches that can be fabricated with control electronics in the thin-film material prior to transfer. The resulting circuit panel is then incorporated into a display panel with a light emitting or liquid crystal material to provide the desired display.

20 Claims, 17 Drawing Sheets

U.S. PATENT DOCUMENTS

| | | | |
|---|---|---|---|
| 4,321,747 | 5/1982 | Takemura et al. | 437/2 |
| 4,393,380 | 7/1983 | Hosokawa et al. | 345/90 |
| 4,409,724 | 10/1983 | Tasch, Jr. et al. | 437/19 |
| 4,429,305 | 1/1984 | Hosokawa et al. | 345/90 |
| 4,582,395 | 4/1986 | Morozumi | 359/57 |
| 4,583,122 | 4/1986 | Ohwada et al. | 348/792 |
| 4,597,636 | 7/1986 | Hoshikawa | 359/82 |
| 4,600,274 | 7/1986 | Morozumi | 359/58 |
| 4,644,338 | 2/1987 | Aoki et al. | 345/92 |
| 4,653,858 | 3/1987 | Szydlo et al. | 359/60 |
| 4,653,862 | 3/1987 | Morozumi | 359/58 |
| 4,654,117 | 3/1987 | Aoki et al. | 156/659.11 |
| 4,655,551 | 4/1987 | Washizuka et al. | 359/83 |
| 4,655,552 | 4/1987 | Togashi et al. | 359/60 |
| 4,660,935 | 4/1987 | Iwashita et al. | 359/54 |
| 4,662,719 | 5/1987 | Di Maria et al. | 359/57 |
| 4,716,403 | 12/1987 | Morozumi | 345/88 |
| 4,727,047 | 2/1988 | Bozler et al. | 117/95 |
| 4,735,495 | 4/1988 | Henkes | 359/42 |
| 4,740,782 | 4/1988 | Aoki et al. | 345/92 |
| 4,769,680 | 9/1988 | Resor, III et al. | 355/43 |
| 4,770,498 | 9/1988 | Aoki et al. | 359/59 |
| 4,772,943 | 9/1988 | Nakagawa et al. | 348/57 |
| 4,774,205 | 9/1988 | Choi et al. | 437/59 |
| 4,782,340 | 11/1988 | Czubatyj et al. | 340/825.83 |
| 4,807,974 | 2/1989 | Hirai | 345/16 |
| 4,808,983 | 2/1989 | Benjamin et al. | 345/90 |
| 4,810,637 | 3/1989 | Szydlo et al. | 437/15 |
| 4,814,830 | 3/1989 | Isohata et al. | 355/54 |
| 4,819,038 | 4/1989 | Alt | 257/10 |
| 4,838,654 | 6/1989 | Hamaguchi et al. | 359/59 |
| 4,838,657 | 6/1989 | Miura et al. | 359/87 |
| 4,846,931 | 7/1989 | Gmitter et al. | 156/633.1 |
| 4,855,255 | 8/1989 | Goodhue | 437/129 |
| 4,859,997 | 8/1989 | Bouron et al. | 345/59 |
| 4,862,153 | 8/1989 | Nakatani et al. | 345/80 |
| 4,863,877 | 9/1989 | Fan et al. | 117/8 |
| 4,870,475 | 9/1989 | Endo et al. | 257/508 |
| 4,870,486 | 9/1989 | Nakagawa et al. | 348/57 |
| 4,878,086 | 10/1989 | Isohata et al. | 355/77 |
| 4,883,561 | 11/1989 | Gmitter et al. | 156/633.1 |
| 4,917,465 | 4/1990 | Conner et al. | 359/41 |
| 4,917,468 | 4/1990 | Matsuhashi et al. | 359/55 |
| 4,930,874 | 6/1990 | Matsumune et al. | 359/59 |
| 4,935,792 | 6/1990 | Tanaka et al. | 257/59 |
| 4,952,031 | 8/1990 | Tsunoda et al. | 359/54 |
| 4,961,629 | 10/1990 | Kato | 359/54 |
| 4,980,308 | 12/1990 | Hyashi et al. | 437/41 |
| 5,013,138 | 5/1991 | Roosen et al. | 359/68 |
| 5,020,881 | 6/1991 | Matsuda et al. | 359/54 |
| 5,053,765 | 10/1991 | Sonehara et al. | 340/815.31 |
| 5,054,887 | 10/1991 | Kato et al. | 359/59 |
| 5,056,895 | 10/1991 | Kahn | 359/87 |
| 5,069,534 | 12/1991 | Hirai | 357/54 |
| 5,073,772 | 12/1991 | Takafuji et al. | 345/89 |
| 5,075,674 | 12/1991 | Katayama et al. | 345/213 |
| 5,076,543 | 12/1991 | Mandai | 353/122 |
| 5,076,666 | 12/1991 | Katayama et al. | 359/59 |
| 5,087,113 | 2/1992 | Sakono et al. | 359/59 |
| 5,095,304 | 3/1992 | Young | 345/92 |
| 5,099,345 | 3/1992 | Kazaki et al. | 359/93 |
| 5,115,232 | 5/1992 | Iizuka | 345/213 |
| 5,117,298 | 5/1992 | Hirai | 359/55 |

OTHER PUBLICATIONS

Akiyama et al., "Growth Of GaAs on Si and ITS Application To FETS and LEDS", *Mat. Res. Soc. Sump. Proc.* vol. 67 (1986):53–64.

Kahn, "High Definiation Projection Display Systems" Flat Information Displays—1990 An Itneractive meeting for Display Users 7 Suppliers to Define & Analyze th Impat of Flat Information Displays on their Products, *Stanford Rexources, Inc. Information Associates.*

"Three–Terminal Devices: Properties & Characteristics", *Stanford Resourcs, Inc.* (1989):114–192.

"Liquid crystal displays (lCD's)", Chapter 2, pp. 29–84.

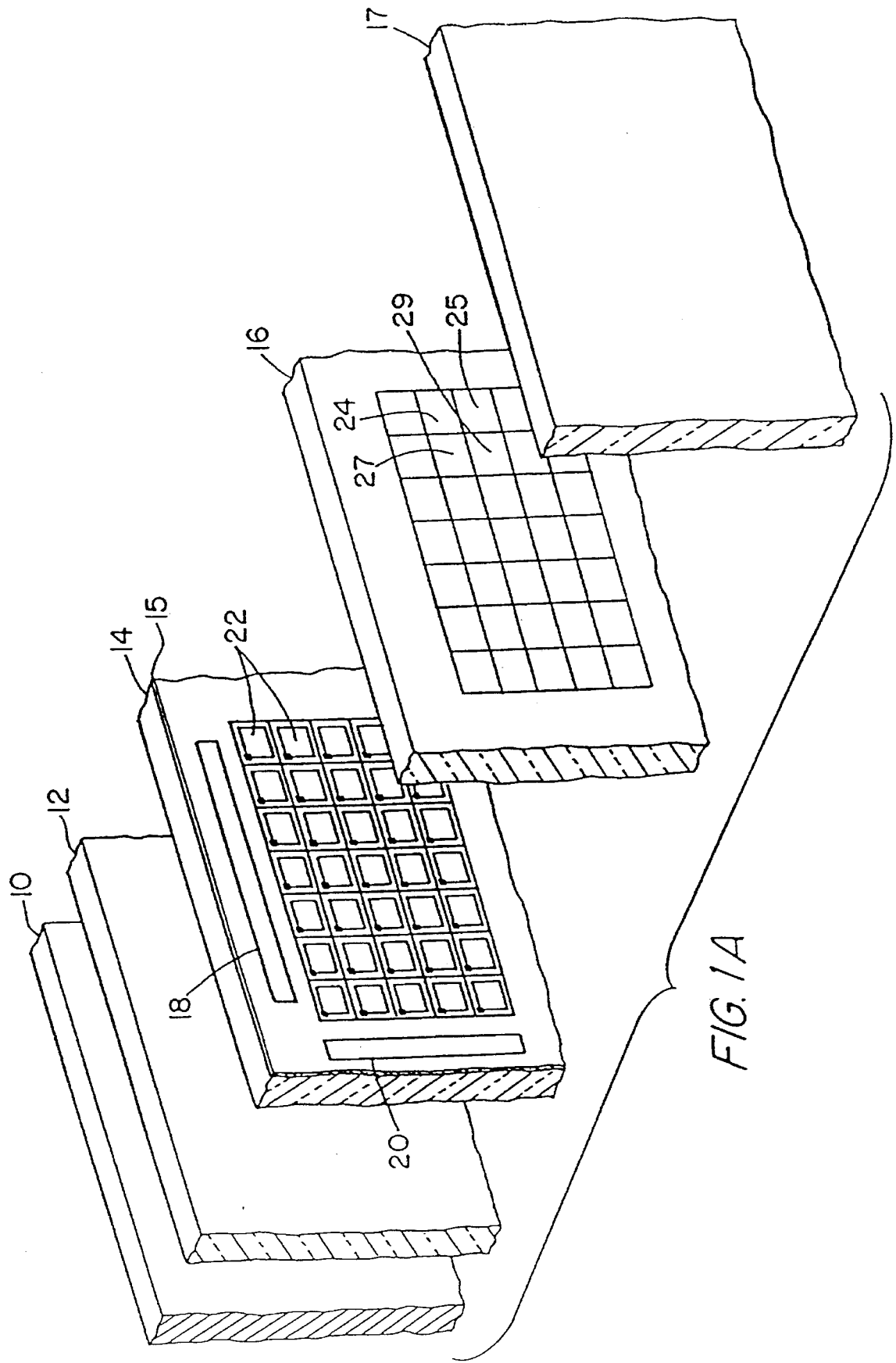

⟨or⟩

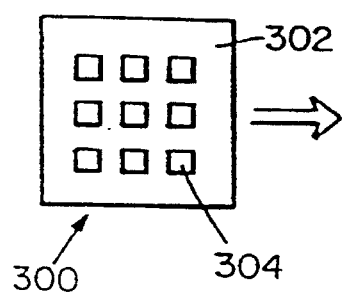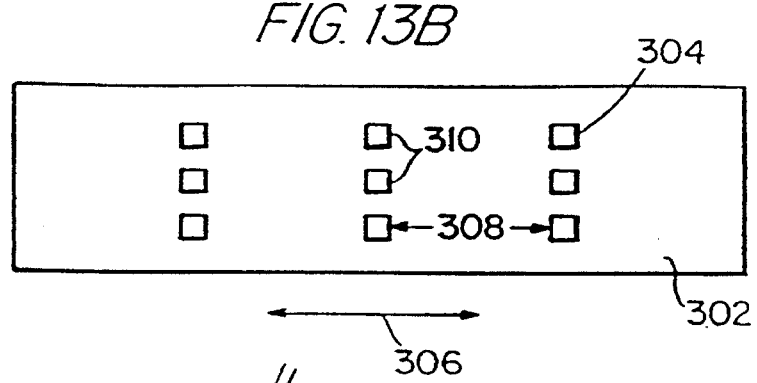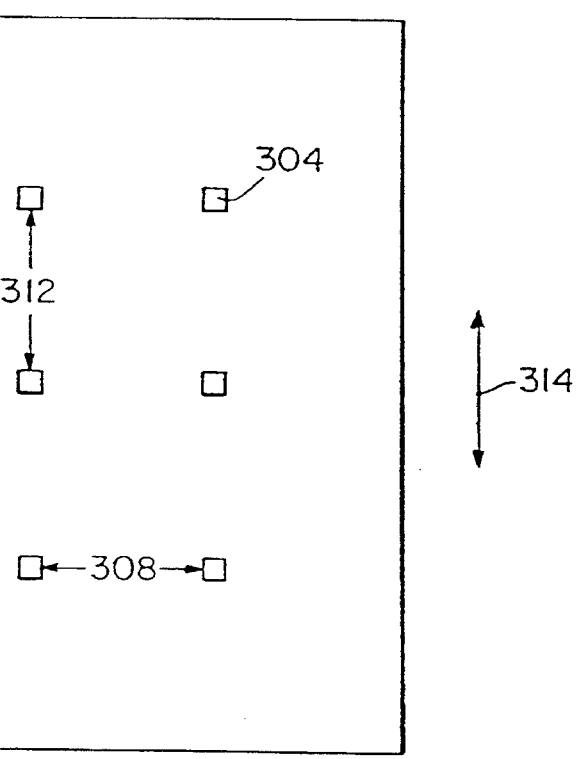

SINGLE CRYSTAL SILICON TRANSISTORS FOR DISPLAY PANELS

This application is a continuation of application Ser. No. 08/225,091 filed Apr. 8, 1994, now U.S. Pat. No. 5,362,671, which is a File Wraper Continuation of Ser. No. 08/085,667 filed on Jun. 30, 1993 (Now Abandoned), which is a File Wrapper Continuation of Ser. No. 07/801,996 filed on Dec. 3, 1991 (Now abandoned), and a Divisional of Ser. No. 07/636,602 filed on Dec. 31, 1990, now U.S. Pat. No. 5,206,749.

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCD's generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across it between the circuit panel and a ground affixed to the filter plate. Thus, when a particular pixel of the display is turned on, the liquid crystal material rotates polarized light being transmitted through the material so that it will pass through the second polarizing filter.

The primary approach to TFT formation over the large areas required for flat panel displays has involved the use of amorphous silicon which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus, the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass which generally restricts further circuit processing to low temperatures.

Thus, a need exists for a method of forming high quality TFTs at each pixel of a panel display having the desired speed and providing for ease and reduced cost of fabrication.

SUMMARY OF THE INVENTION

The present invention relates to panel displays and methods of fabricating such displays using thin-films of essentially single crystal silicon in which transistors are fabricated to control each pixel of the display. For a preferred embodiment, the thin-film or transistor array is transferred onto an optically transmissive substrate such as glass or transparent organic films. In this embodiment, the thin-film single crystal silicon is used to form a pixel matrix array of thin-film transistors which actuate each pixel of an LCD. CMOS circuitry that is highly suitable for driving the panel display can be formed in the same thin-film material in which the transistors have been formed. The circuitry is capable of being fully interconnected to the matrix array using thin-film metallization techniques without the need for wires and wirebonding.

Each transistor, by application of an electric field or signal, serves to control the optical transmission of light from or through an adjacent material or device. For the purposes of this application the transistor and the adjacent material or device through which light from a source is transmitted is refered to as a light valve. Thus, each pixel of the panel display can be an independently controlled light valve. Examples of such light valves include LCDs or any liquid or solid state material whose light transmitting characteristics can be altered with an electric field or signal and which can be configured to provide a dense pixel array. The present devices and related methods of fabrication satisfy all of the requirements of large scale flat panel to produce highly defined color images. The transistors of switches can be paired with electroluminescent display elements (ELDs) or light emitting diodes (LEDs) to provide a display.

A preferred embodiment of the present invention utilizes large area semiconductor films, separates the films from the processing substrate, and mounts them on glass or other suitable optically transmissive materials. Films of single crystal silicon with thicknesses on the order of 2 microns or less, have been separated from epitaxial substrates, and the films have been mounted on glass and ceramics. Functional p-n junction devices such as field effect transistors ("FETs") are at least partially fabricated prior to separation and then transferred to glass. Various bonding procedures can be used for mounting on substrates including adhesives, electrostatic bonding, Van der Waal's forces or a eutectic alloy for bonding. Other known methods can also be utilized.

A preferred embodiment of the process comprises the steps of forming a thin essentially single crystal Si film on a release substrate, fabricating an array of pixel electrodes and thin-film enhancement mode, transistors, and associated CMOS circuitry on the thin film. Each transistor is electrically connected to one of the pixel electrodes such that each pixel can be independently actuated by one of the transistors. The CMOS circuitry can be used to control pixel actuation and the resulting image or images that are displayed. Device fabrication can be initiated while the thin-film is still attached to the release substrate by formation of source, drain, channel and gate regions, and interconnection with pixel electrodes. By substantially completing device processing prior to transfer to the final panel substrate, a low temperature glass or polymer can be used. Alternatively, all or a portion of device fabrication can occur after release, or upon transfer of the processed film to the glass or plastic plate. After transfer, integration with color filters and liquid crystal materials completes the panel for an embodiment employing an LCD.

Preferred methods of thin-film formation processes employ silicon-on-insulator (SOI) technology where an essentially single crystal film is formed on an insulating substrate from which it can be released. For the purposes of the present application, the term "essentially single crystal" means a film in which a majority of crystals extend over a cross-sectional area, in the plane extending laterally through the film, of at least $0.1 \text{ cm}^2$ and preferably in the range of 0.5–1.0 cm² or more. Such films can be formed using known techniques, on sapphire, SiO₂, carbon and silicon carbide substrates, for example.

SOI technology generally involves the formation of a silicon layer whose crystal lattice does not match that of the underlying substrate. A particular preferred embodiment uses Isolated Silicon Epitaxy (ISE) to produce a thin film of high quality Si on a release layer. This process can include the deposition of a non-single crystal material such as amorphous or polycrystalline silicon on the release layer which is than heated to crystallize the material to form an essentially single crystal silicon. The use of a release layer enables the film and circuit release using oxides beneath the active layer that can be etched without harm to the circuits.

In a preferred embodiment the entire substrate on which the epitaxial film has been formed is removed by an etch back procedure.

Alternatively, methods of chemical epitaxial lift-off, a process for transferring semiconductor material to glass or other substrates, can be applied to large area sheets of the desired semiconductor material. These or other release methods can be used to remove any thin-film single crystal material from a growth substrate for transfer onto substrates for circuit panel fabrication.

The present invention includes CMOS circuit and pixel electrode formation in a recrystallized silicon film that is then, secured to a second transfer substrate, removed from the starting wafer or substrate, and mounted on the glass or other suitable substrate to form the circuit panel. Alternatively, one can first form the circuits, bond the circuits to glass, and then separate the circuits from the substrate. The pixels are positioned in rows and columns having a planar geometry. The order of the fabrication steps allows the use of conventional fast CMOS (or other) logic onboard the glass, since the high temperature processing for these circuits are performed prior to transfer.

Another preferred embodiment involves the fabrication of a discrete array of transistor elements, transferring these elements onto a stretchable substrate which either contracts or expands to provide the desired spacing or registration of the discrete elements and then transferring these elements onto a final substrate that is including in the display panel.

The above, and other features of the invention including various novel details of construction and combination of parts, will now be more particularly described with reference to the accompanying drawings and that pointed out in the claims. It will be understood that the particular panel display and the methods used in fabricating those panels which embody the invention are shown by way of illustration only and not as a limitation of the invention. The principal features of this invention can be employed in various embodiments without departing from the scope of the invention.

BRIEF DESCRIPTION OF THE DRAWINGS

FIG. 1A is an exploded perspective view of a flat panel display in accordance with the invention.

FIGS. 13A–13C schemztically illustrate a preferred method of transfer in accordance with the invention.

DETAILED DESCRIPTION

Figure 1B:
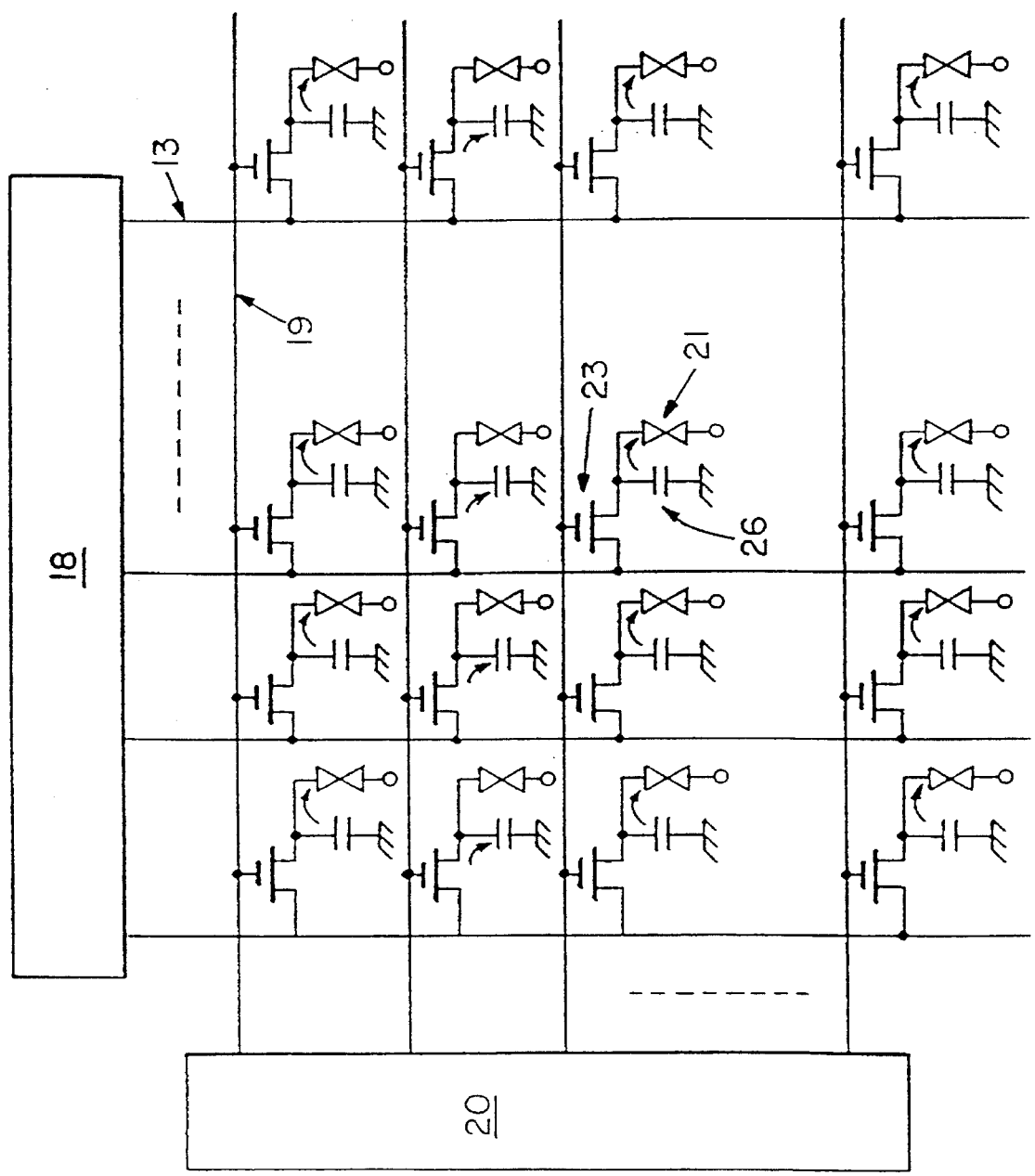
FIG. 1B is a circuit diagram illustrating the driver system for a preferred embodiment of the invention.

A preferred embodiment of the invention is illustrated in the perspective view of a panel display in FIG. 1. The basic components of the display include a light source 10 that can be white or some other appropriate color, a first polarizing filter 12, a circuit panel 14, a filter plate 16 and a second polarizing filter 17, which are secured in a layered structure. A liquid crystal material (not shown) is placed in a volume between the circuit panel 14 and the filter plate 16. An array of pixels 22 on the circuit panel 14 are individually actuated by a drive circuit having first 18 and second 20 circuit components that are positioned adjacent the array such that each pixel can produce an electric field in the liquid crystal material lying between the pixel and a counterelectrode secured to the color filter plate 16. The electric field causes a rotation of the polarization of light being transmitted across the liquid crystal material that results in an adjacent color filter element being illuminated. The color filters of filter plate system 16 are arranged into groups of four filter elements such as blue 24, green 25, red 27, and white 29. The pixels or light values associated with filter elements 24, 25, 27, 29 can be selectively actuated to provide any desired color for that pixel group.

Other preferred embodiments employ the use of a solid state material to form a light valve for each pixel. A light emitting material such as an electroluminescent film or any material whose optical transmission properties can be altered by the application of an electric field can be used to supply the light value of the present invention.

A drive circuit that can be used to control the display on the panel is illustrated in FIG. 1B. Circuit 18 receives an incoming signal and sends a signal to the pixels through buses 13. Circuit 20 will scan through buses 19 to turn on the individual transistors 23 which charges capacitor 26 in each pixel. The capacitor 26 sustains the charge on the pixel electrode and the liquid crystal 21 until the next scan of the array. The various embodiments of the invention may, or may not, utilize capacitors with each pixel depending upon the type of display desired.

FIGS. 2A–2L illustrate the use of an Isolated Silicon Epitaxy (ISE) process, to form silicon-on-insulator (SOI) films in which circuit panel circuitry is formed. Note that any number of techniques can be employed to provide a thin-film of single crystal Si. An SOI structure, such as that shown in FIG. 2A, includes a substrate 30 and an oxide 34 (such as, for example, $SiO_2$) that is grown or deposited on the substrate 30. A thin single crystal layer of silicon is formed over the oxide 34. The oxide (or insulator) is thus buried beneath the Si surface layer. For the case of ISE SOI structures, the top layer is a substantially single-crystal recrystallized Silicon, from which CMOS circuits can be fabricated. The use of a buried insulator provides devices having higher speeds than can be obtained in conventional bulk (Czochralski) material. Circuits containing in excess of 1.5 million CMOS transistors have been successfully fabricated in ISE material.

Figure 2A:
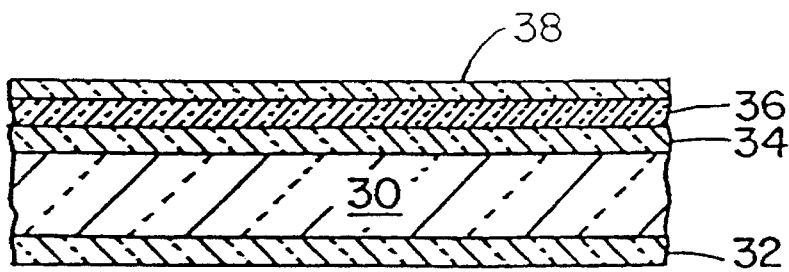
FIGS. 2A–2L is a preferred process flow sequence illustrating the fabrication of a circuit panel for a flat panel display.
Figure 2B:
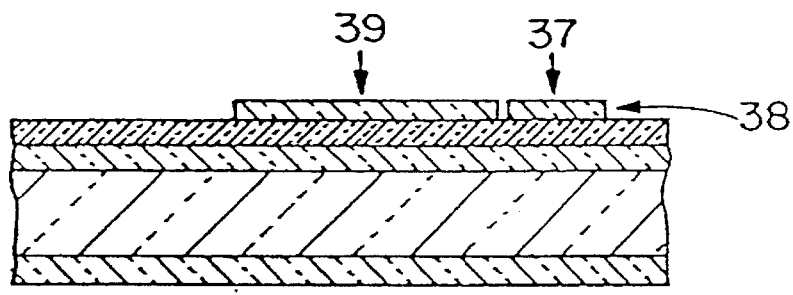
Figure 2C:
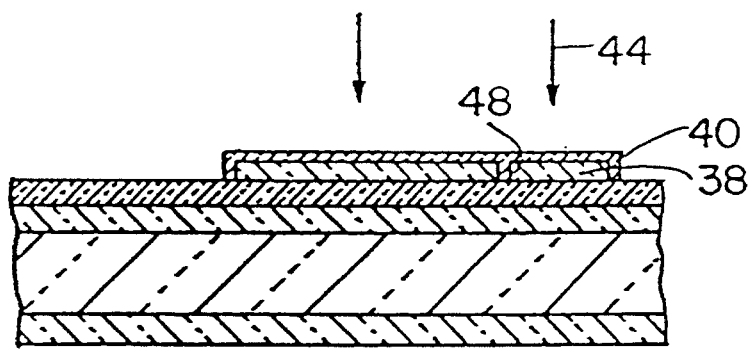

As shown in FIG. 2B, the film 38 is patterned to define a transistor region 37 and a pixel electrode region 39 for each pixel. An oxide layer 40 is then formed over the patterned regions including channel 48 between the two regions 37, 39 of each pixel. The intrinsic crystallized material 38 is than implanted 44 (at FIG. 2C) with boron or other p-type dopant to provide a n-channel device (or alternatively, an n-type dopant for an p-channel device).

Figure 2D:
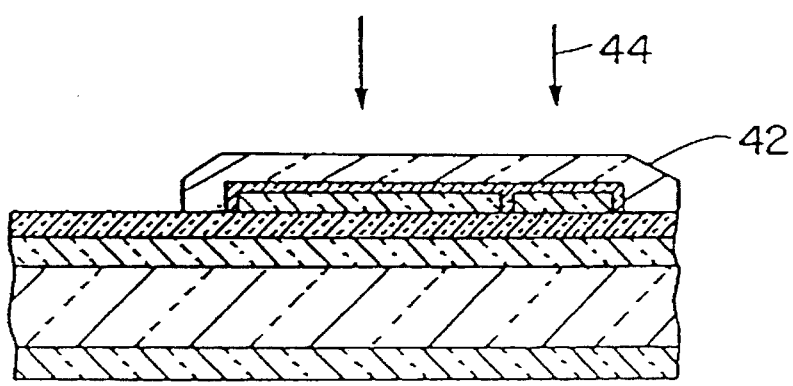
Figure 2E:
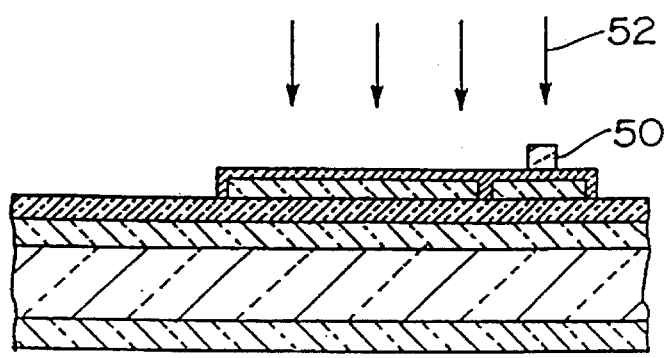
Figure 2F:
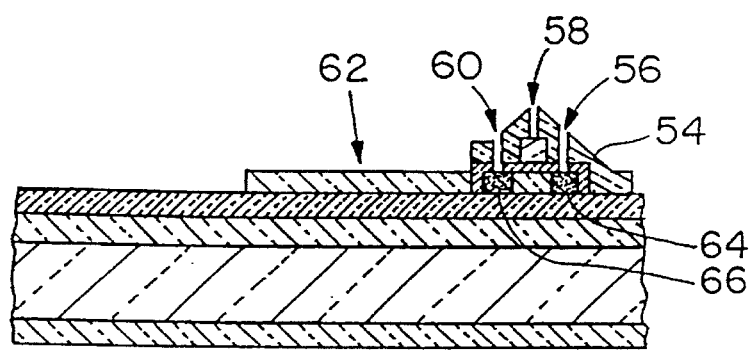
Figure 2G:
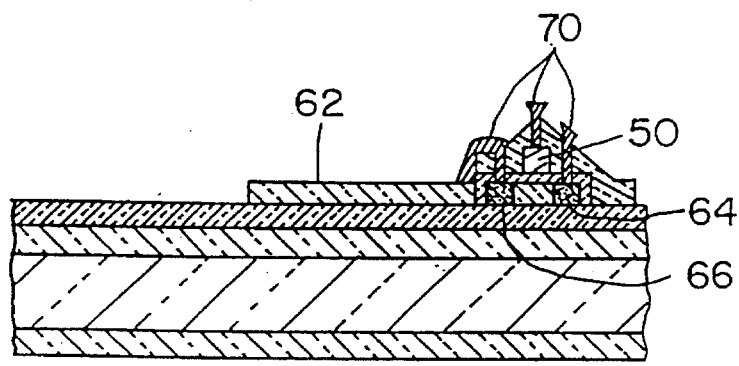
Figure 2H:
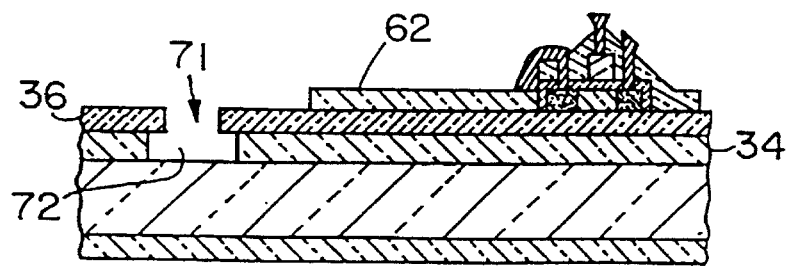

A polycrystalline silicon layer 42 is than deposited over the pixel and the layer 42 is then implanted 46, as seen in FIG. 2D, with an n-type dopant to lower the resistivity of the layer 42 to be used as a gate. The polysilicon is patterned to form the gate 50, as seen in FIG. 2E, which is followed by a large implant 52 of boron to provide p+ source and drain regions for the transistor. As shown in FIG. 2F, an oxide 54 is formed over the transistor and openings 60, 56, 58 are formed through the oxide 54 to contact the source 66, the drain 64, and the gate, respectively. A patterned metalization 70 of aluminum, tungsten or other suitable metal is used to connect the exposed pixel electrode 62 to the source 60 (or drain), and to connect the gate and drain to other circuit panel components.

A second fabrication procedure is one of the substrate release processes that have been developed to form thin (1 to 5 micron) films of processed silicon bonded to glass; these films contain active semiconductor devices such as FETs that are partially of completely fabricated prior to transfer. The crystallization and release procedures including the cleavage of laterally grown epitaxial films for transfer (CLEFT) approach are described more fully in U.S. Pat. No. 4,727,047 incorporated herein by reference. The chemical epitaxial lift-off (GEL) approach is described more fully in U.S. Pat. Nos. 4,846,931 and 4,883,561. Both of the CLEFT and CEL techniques permit the reuse of the substrate, leading to reduced cost compared to other approaches in which the substrates are consumed. By combining thin film release techniques with SOI wafers, we will be able to form the required high quality films and circuits on glass.

The foregoing indicates that CEL processes can be limited by the lateral distance that is required for the HF (or other etchant) undercut of the release layer. The key to large area panels using CEL is the release of patterned devices and/or circuits rather than complete large-area films, because the circuits or devices have unused areas that can be used as vertical channels through the film to allow the etch to reach the release layer. This approach is illustrated in FIGS. 2H–2L. To remove the circuit from the release substrate a first opening 70 (in FIG. 2H) is formed in an exposed region of layer 36 that occurs between pixels. A second larger portion of layer 34 is than removed to form cavity 72 such that a portion of layer 36 extends over the cavity 72.

Figure 2I:
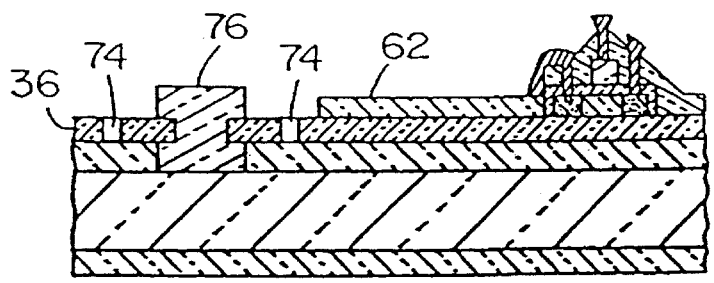
Figure 2J:
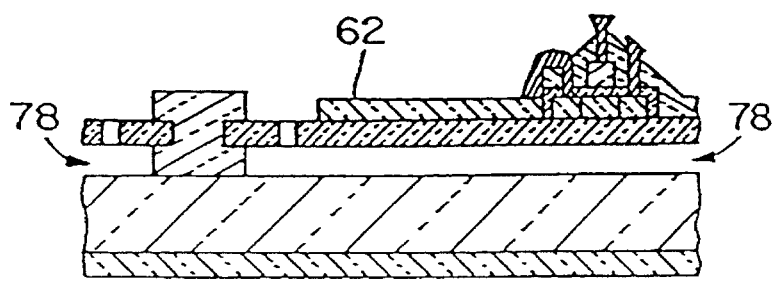
Figure 2K:
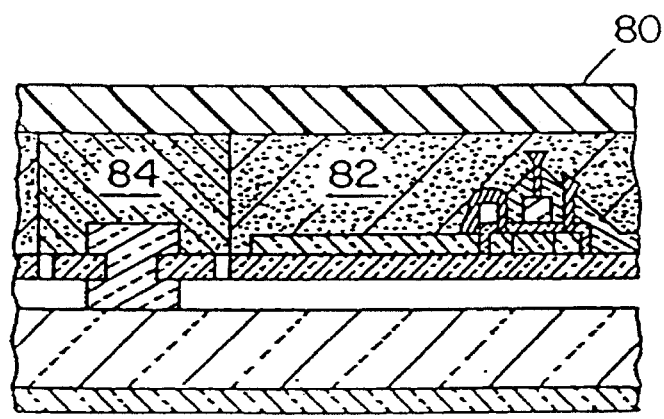

In FIG. 2I, a support post 76 is formed to fill cavity 72 and opening 70, and which extends over a portion of layer 36. Openings or via holes 74 are then provided through layer 36 such that an etchant can be introduced through holes 74, or lateral openings 78, to remove layer 34 (see FIG. 2J). The remaining insulating layer 36 and the circuitry supported thereon is now held in place relative to substrate 30 with support posts 76.

An epoxy that can be cured with ultraviolet light is used to attach an optically transmissive substrate 80 to the circuitry, and layer 36. The substrate 80 is than patterned such that regions of epoxy 84 about the posts 76 remain uncured while the remaining epoxy 82 is cured (see FIG. 2K). The substrate 30 and posts 76 are removed to provide the structure shown in FIG. 2L, which is than processed to provide the desired display panel.

Note that the UV-cured adhesive (or tape) can be patterned to protect the circuits where necessary, and HF can be used to reach the remaining the release layer.

Note that where tape is used, tape provides support to the circuits after release. Large area GaAs devices containing films have been fabricated in this way, and these have been released to form devices from entire wafers on one tape. The released circuits can be remounted on the glass and the other elements of the liquid crystal display panel. Transparent adhesives are the preferred method of mounting.

Figure 2L:
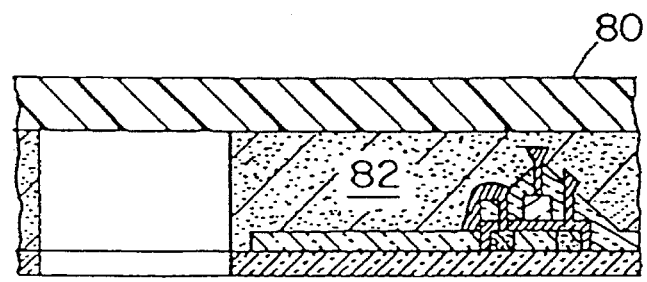

To form the final display panel the circuit panel shown in FIG. 2L is etched leaving the desired pixel elements exposed. Insulation and alignment layers, spacers, a sealing border and bonding pads for connections as added onto the circuit panel. A screen printing process can be used to prepare the border. The plate containing the color filters and the counterelectrode is sealed to the circuit panel with the sealing border after insertion of spacers. The display is filled with the selected liquid crystal material via a small filling hole or holes extending through the border. This filling hole is then sealed with a resin or epoxy. First and second polarizer films or layers are than bonded to both sides and connectors are added. Finally, a white light source 114, or other suitable light source, is coupled to polarize 112.

Figure 3:
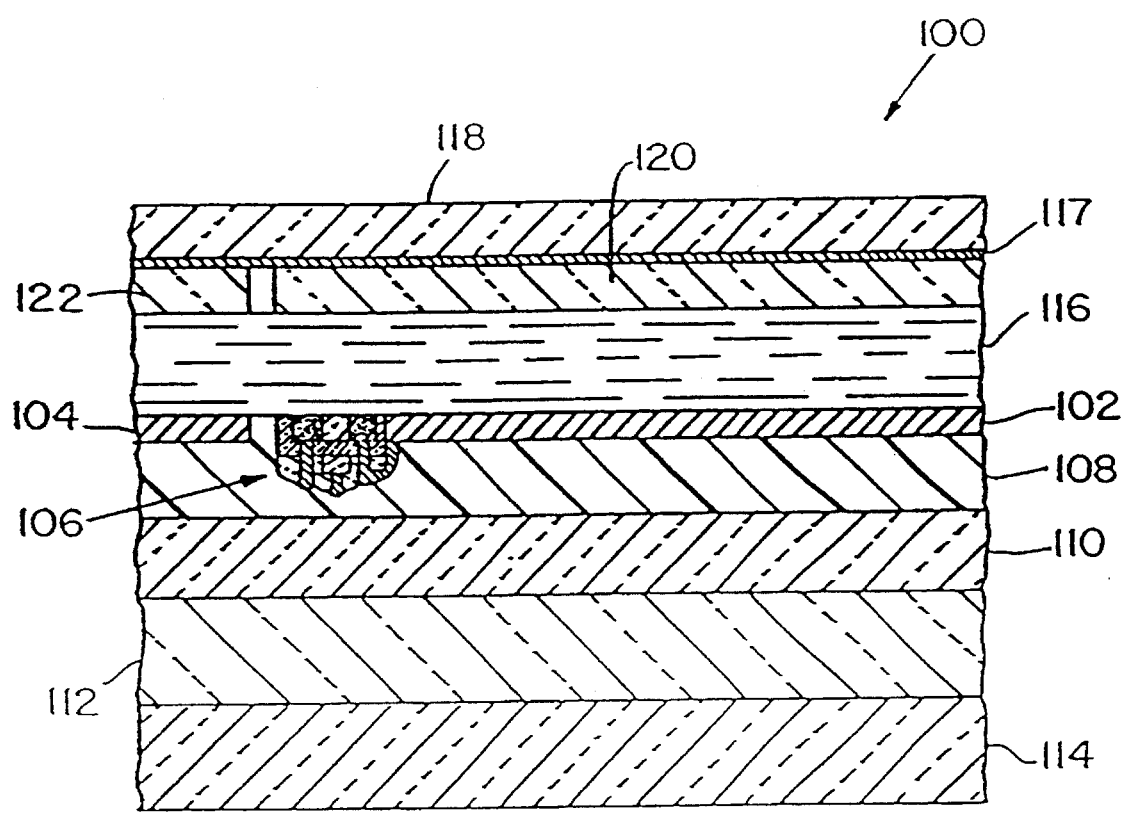
FIG. 3 is a cross-sectional view of a preferred embodiment of the display panel.

A cross-sectional view of the resulting device is shown in FIG. 3 wherein pixel electrodes 102 and 104 are laterally spaced from each other. Each pixel 102, 104 will have a transistor 106 and a color filter 120, 122 associated therewith. Polarizing elements 112, 118 are positioned on opposite sides of the structure this also includes bonding element or adhesive 108 and optically transmissive substrate 110, such as glass or plastic. Layer 108 can be a transparent epoxy or a low temperature glass that can have a thickness of 2–10 microns.

The CLEFT process permits the separation of a thin single-crystal films, grown by chemical vapor deposition (CVD), from a reusable homoepitaxial substrate. Unlike the CEL process, in the CLEFT process the circuits or devices are first bonded to glass and after mounting the separation is made between the circuits and the substrate.

The films removed from the substrate by CLEFT are essentially single-crystal, of low defect density, are only a few microns thick, and consequently the circuit panel has little weight and good transmission characteristics. For the purposes of the present application, the term "essentially single crystal" means a film in which a majority of crystals extend over a cross sectional area in a plane of the film of at least $0.1$ cm$^2$, and preferably in the range of $0.5–1.0$ cm$^2$ or more.

The CLEFT process, illustrated in U.S. Pat. No. 4,727,047 involves the following steps: growth of the desired thin film over a release layer (a plane of weakness), formation of metallization and other coatings, formation of a bond between the film and a second substrate such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon the lateral epitaxy is accomplished by the ISE process or other recrystallization procedures. Alternatively, other standard deposition techniques can be used to form the necessary thin-film essentially single crystal material.

One of the necessary properties of the material that forms the release layer is the lack of adhesion between the layer and the semiconductor film. Since a weak plane has been created by the release layer, the film can be cleaved from the substrate without any degradation. The release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated resulting in simpler handling as compared to UV-cured tape.

In the ISE process, the oxide film is strongly attached to the substrate and to the top Si film which will contain the circuits. For this reason, it is necessary to reduce the strength of the bond chemically. This technique involves a release layer that is preferentially dissolved with an etchant without complete separation, to form a plane of weakness in the release layer. The films can then be separated mechanically after the glass is bonded to the circuits and electrodes.

Mechanical separation is accomplished as follows: The upper surface of the film is bonded with a transparent epoxy to a superstrate such as glass. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing is completed on the back surface of the film. Note that since the device remains attached to a superstrate, the back side can be subjected to standard wafer processing, including photolithography.

The method further involves the preparation of single crystal films, with (Si substrate) and without (foreign substrates) seeding. For the case of seeded Si films, the standard recrystallization process is employed. To optimize the bottom oxide or nitride layer for release purposes no seeding is used.

Figure 4:
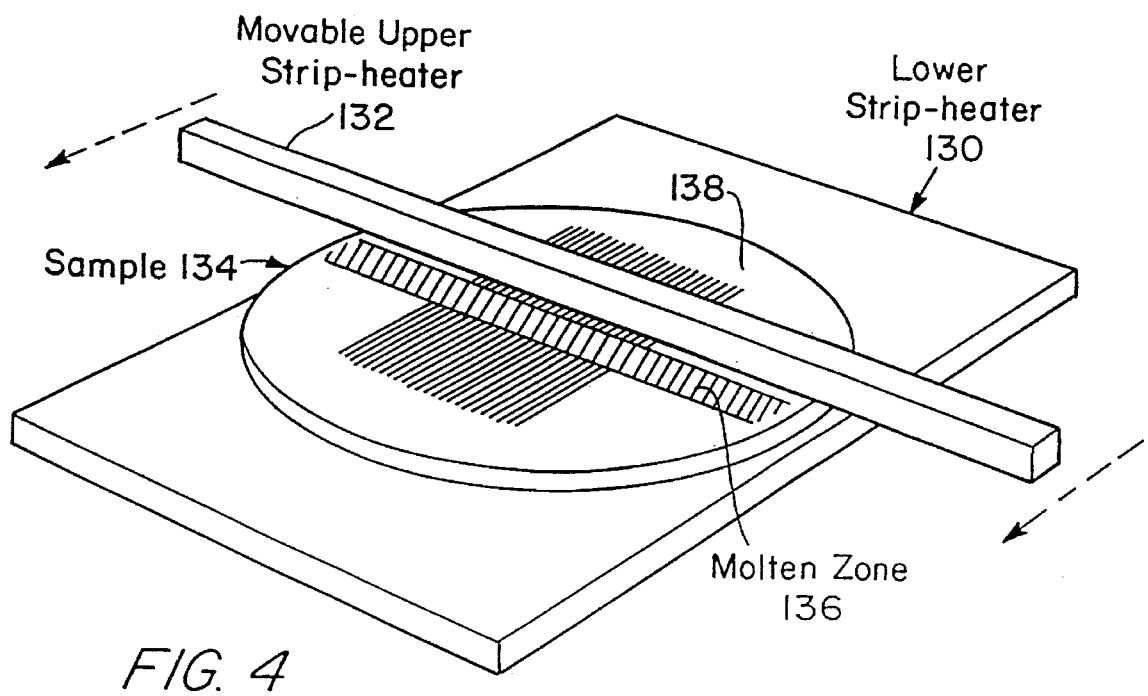
FIG. 4 illustrates in a perspective view a preferred embodiment of a system used for recrystallization.

In one embodiment of the recrystallization system, shown schematically in FIG. 4 the substrate temperature is elevated to near the melting point by a lower heater 130. An upper wire or graphite strip heater 132 is then scanned across the top of the sample 134 to cause a moving melt zone 136 to recrystallize or further crystallize the polycrystalline silicon. In the standard process on Si, the lateral epitaxy is seeded from a small opening through the lower oxide, and the resultant single crystal film has the orientation of the substrate. Capping layer 138 is deposited over the polycrystalline material prior to crystallization.

Figure 5A:
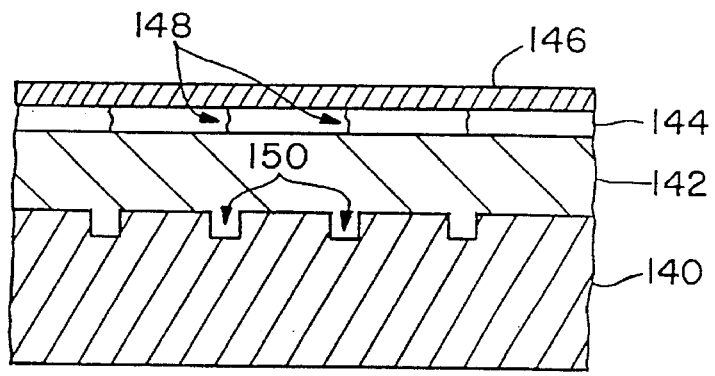
FIG. 5A illustrates the use of a patterned release layer to entrain boundaries in a crystallized material.

Grain boundary entrainment can be used by patterning either the release oxide or the cap layer to introduce a modulation in the thermal gradients in the regrowth region. This modulation in the temperature field changes the location of the melt front and entrains the boundaries in predictable locations. Patterning of the release oxide 142 is shown in FIG. 5A. In this embodiment the substrate 140 has grooves 150 which are filled with the release oxide 142. Owing to this entrainment of boundaries 148 in the crystallized material 144 that can extend between the cap 146 and the release layer 142, the Si circuits or electrodes can be located in regions of high quality. Metallization and other features can be located over subgrain boundaries.

As shown, a preferable technique is to pattern the reusable substrate with the necessary entrainment structure. Once patterned in this way, the reusable substrate would in principal not require repatterning. In such a scheme the entraining grooves are provided with a material of sufficient thickness to entirely fill the grooves. The material in the grooves could for example, comprise planarized $Si_3N_4$, while the release layer could comprise further deposition of $SiO_2$. Alternatively, the grooves could be filled entirely with $SiO_2$; the grooves could then function as channels for the release etch.

Figure 5B:
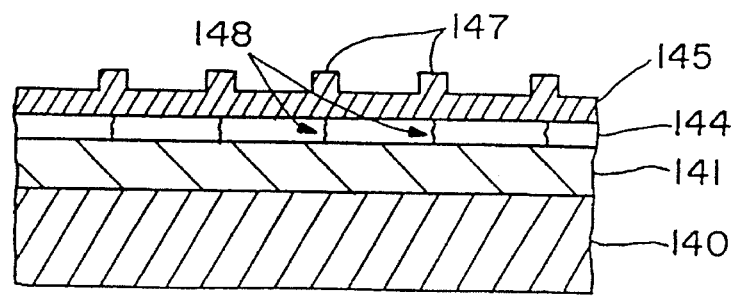
FIG. 5B illustrates the use of a patterned capping layer to entrain boundaries.

A second approach involves patterning the cap lever 145 after cap deposition, as shown in FIG. 5B. Patterned ridges 147 of the cap 145 overlie boundaries 148 in the recrystallized material that can extend between the cap 145 and release layer 141. A third approach would be to pattern the polycrystalline silicon layer.

Capping layers can be used with foreign substrates. The capping layer must be adherent throughout the thermal cycle, but must be removable for device processing. A baseline cap works well for smooth Si substrates, but the patterned layers necessary for entrainment can require new films.

Figure 6A:
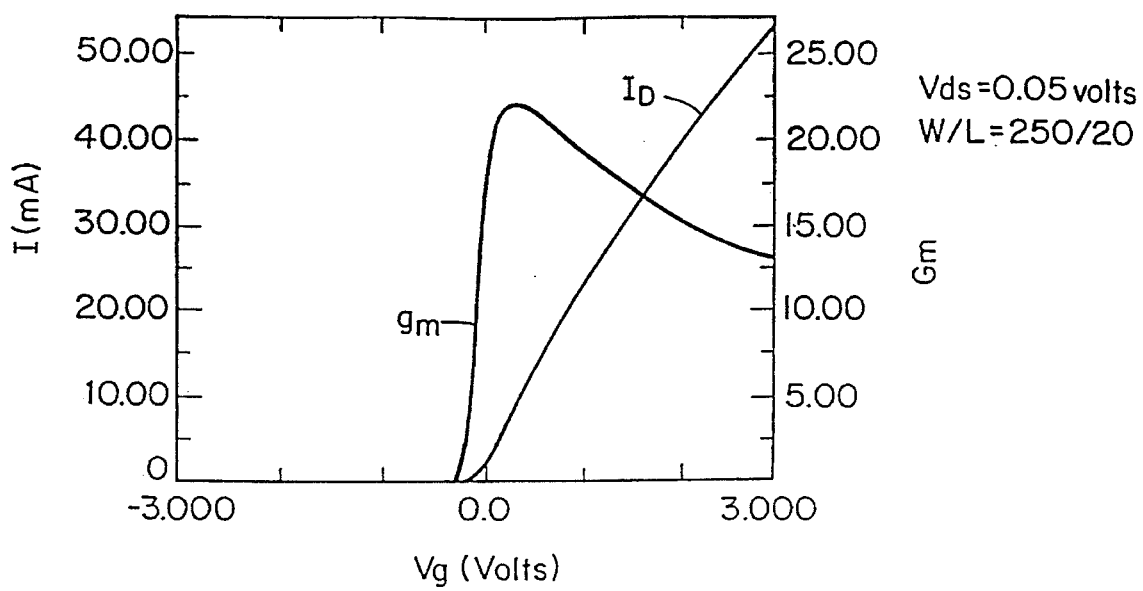
FIG. 6A illustrates the drain current and transconductance characteristics for a MOSFET prior to transfer to glass in accordance with the invention.
Figure 6B:
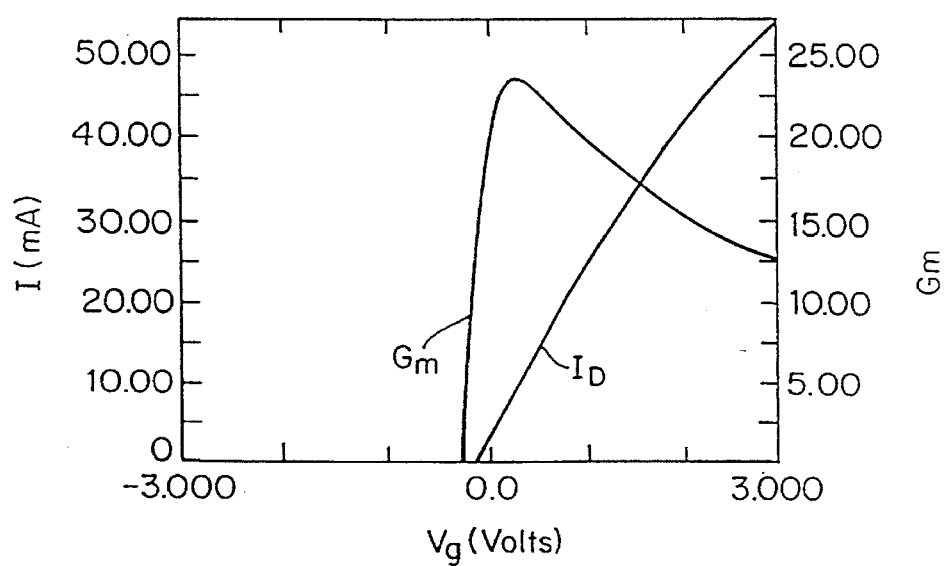
FIG. 6B illustrates the drain current and transconductance characteristics for the MOSFET of FIG. 6A after transfer to glass.

FIGS. 6–8 illustrate the electrical characteristics of a MOSFET made in accordance with the invention before and after transfer onto a glass substrate. FIG. 6A graphically depicts the drain current $I_D$ and the transconductance $G_M$ as a function of gate voltage $V_G$ in the linear region, where the drain-source voltage is 50 mV, for a MOSFET prior to transfer to glass. The MOSFET has a width-to-length ratio of 250 μm/20 μm and a gate oxide thickness of 890 A in a 0.5 μm thick recrystallized silicon material. FIG. 6B shows the drain current $I_D$ and transconductance $G_M$ of the same device after transfer to glass.

Figure 7A:
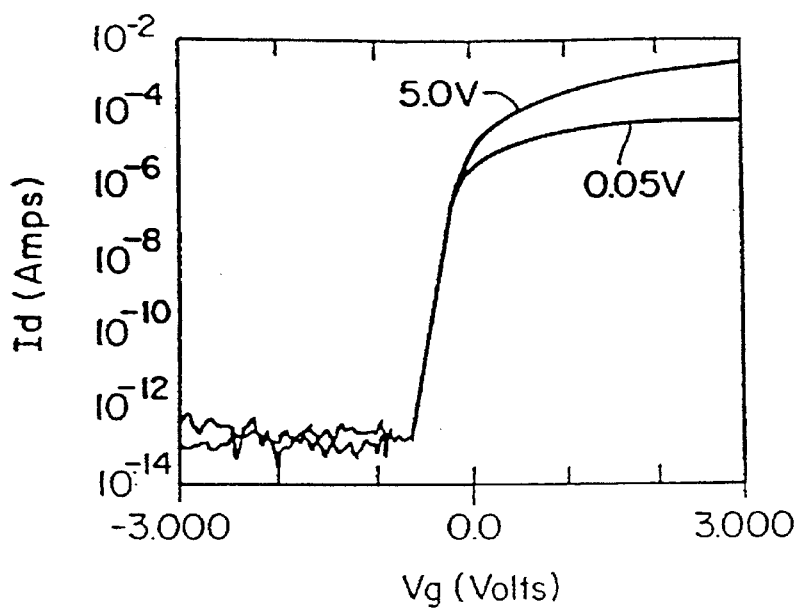
FIG. 7A illustrates the drain current of the device in FIG. 6A plotted on a logarithmic scale at two different drain voltages.

FIG. 7A graphically illustrates the drain current of the device of FIG. 6A plotted on a logarithmic scale at two drain-source voltages $V_{DS}$=50 mV and $V_{DS}$=5 V.

Figure 7B:
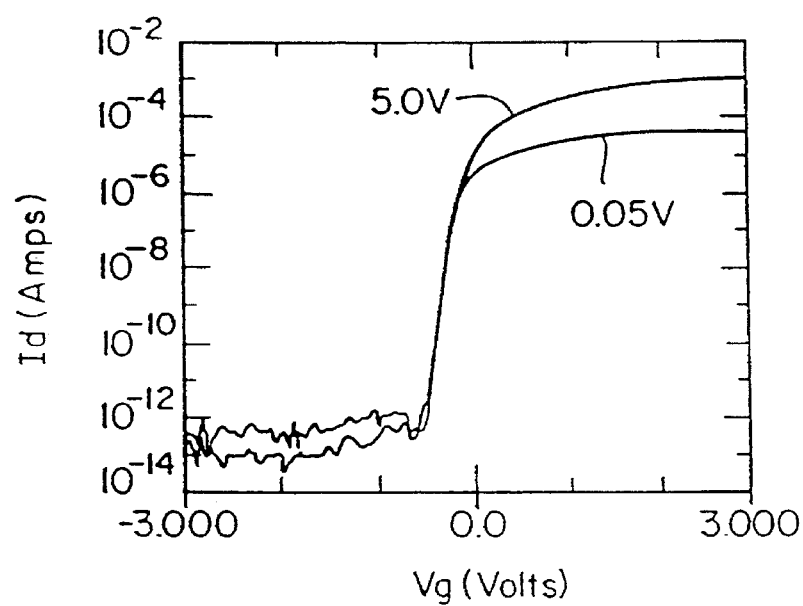
FIG. 7B illustrates the drain current of the device in FIG. 6B plotted on a logarithmic scale at two different drain voltages.

FIG. 7B graphically illustrates the drain current of the device in FIG. 6B poltted on a logarithmic scale at drain-source voltages of $V_{DS}$=50 mV and $V_{DS}$=5 V.

Figure 8A:
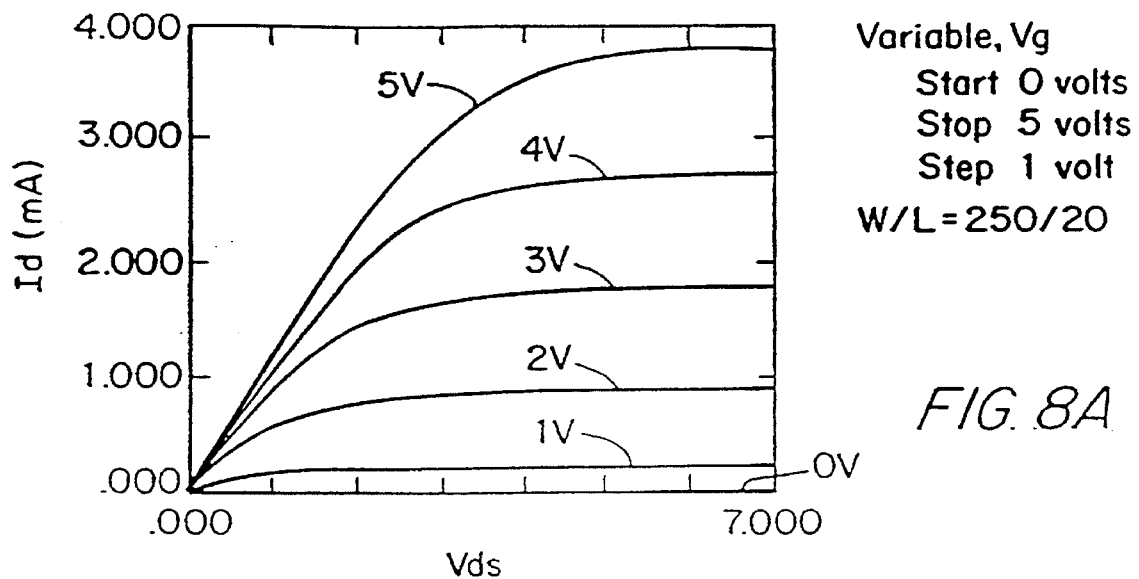
FIG. 8A illustrates the drain current output of the device of FIG. 6A with the gate voltage varying between 0 and 5 volts.

FIG. 8A graphically illustrates the drain current $I_D$ as a function of drain-source voltage of the device of FIG. 6A at gate voltages of $V_{GS}$=0, 1, 2, 3, 4 and 5 volts.

Figure 8B:
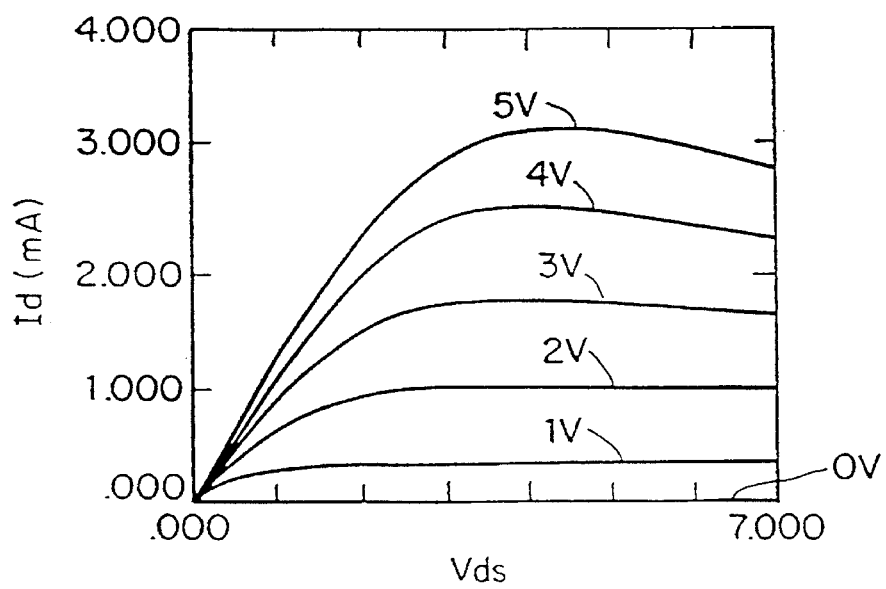
FIG. 8B illustrates the drain current output of the device of FIG. 6B with the gate voltage varying between 0 and 5 volts.

FIG. 8B graphically illustrates the drain current $I_D$ as a function of drain-source voltage of the device of FIG. 6B at gate voltages of $V_{GS}$=0, 1, 2, 3, 4 and 5 volts.

For the CEL approach, a further embodiment involves remounting of the released films on glass plates. The application method insures uniform intimate contact between the thin-film semiconductor and the adhesive, yet must not crack or introduce other defects in the thin films.

Methods involve the application of Apiezon W wax to the frontside of the layer to be separated. The stress in the wax imparts a curvature to the lifting layer thereby allowing the etching fluid access to the etching front. Access to the etching front is achieved only from the outer edge of the total area being lifted off.

This process is of limited use for applications involving large area liftoff, however, due to long liftoff times that can extend up to hours or days for areas larger then 2 cm×2 cm. Curvature is required to increase etchant access to the etching front. However, the curvature necessary for liftoff is caused by a low temperature wax so that no high temperature processing can be done on the backside of the lifted area. Present samples are often cleaved to size, not allowing for substrate reuse. The wax application process is automated and patternable to allow for substrate reuse in applications where this procedure is preferred. This process is useful only for individual small areas that don't require backside processing.

Figure 9A:
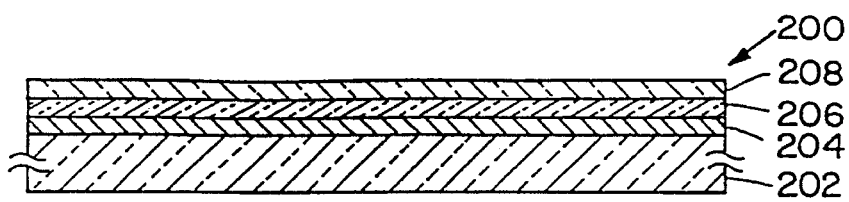
FIGS. 9A–9C are a series of cross-sectional diagrams illustrating a lift-off process in accordance with the inventor.
Figure 9B:
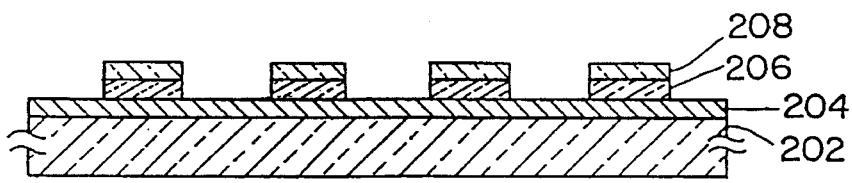
Figure 9C:
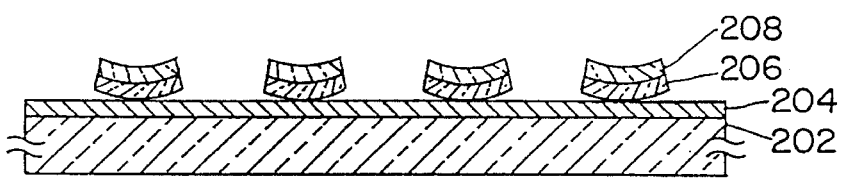

Another embodiment of the invention involves using a combination of thin or thick film materials with different coefficients of expansion to replace the black wax in the standard liftoff process. This process is illustrated in FIGS. 9A–9C. By using the correct temperature the curvature needed for liftoff is achieved due to the differential stresses in the layers. A single layer can be used if it has the correct expansion coefficient with respect to the material being lifted off. This method allows for support layers that impart the correct curvature at the liftoff temperature, lay flat at room temperature, and also support the film during backside processing.

This embodiment of the invention will now be described in connection with structure 200 of FIGS. 9A–9C. A substrate 202, which can comprise any suitable substrate material upon which epitaxial layers or devices can be formed, is provided. A release layer 204 is grown, preferably by CVD, on substrate 202. For a thin-film silicon releasable layer, an SiO$_2$ layer can be used as previously described.

A semiconductor layer structure 206 is formed on release layer 204, also by OMCVD or other previously described methods. Structure 206 preferably comprises materials arranged for the fabrication of an array of transistors in accordance with the invention.

By using CVD, for example, structure 206 can be made very thin, i.e., less than about 5 microns and, preferably, less than 2 microns, with the contact layer being less than 0.1 micron thick.

The necessary dopants are typically introduced by diffusion after the growth processes to define source, drain and channel regions. Next, the structure 206 is processed on the front, or top side, using conventional techniques to form gates and metal contacts where each pixel is to be located and buss bars and bonding pads, as required.

In a first lift-off embodiment, a coating 208 is then formed on the front side processed structure 206 (FIG. 9A). The coating consists of a combination of thick or thin film materials with different thermal coefficients of expansions. For example, coating 208 can comprise a nitride, metal. bi-metal or a glass stressed coating. Contact metallization (not shown) can also be applied at this time on the contact layer.

The coating layer 208 and structure 206 are then patterned using conventional photolithography and the coating material 208 and structure 206 is removed in predetermined areas down to release layer 204 as shown in FIG. 9B, by etching with a suitable selective etchant. The above steps are performed at a predetermined temperature which is sufficiently low no significant thermal stress between the coating materials of coating 208 is produced. Next, the temperature is elevated to a sufficient degree, causing thermal stress in the coating 208. While at this elevated temperature the structure is exposed to a release etchant (See FIG. 9C).

The release etchant eventually etches the release layer 204 sufficiently to allow separated device structures 206 supported by the coating 208 to be removed. These structures are then brought down to a lower temperature at which the thermal stress is relieved to allow the discrete devices to lay flat for subsequent backside processing.

This process provides a significant advantage over the Gmitter et al. black wax process in that it enables the discrete chips to lay flat for backside processing and the support structure is formed of materials, such as glass, which are impervious to the backside processing temperatures.

Two different procedures can be used to achieve wafer scale liftoff. The first method involves the etching of the entire substrate on which the film to be transferred has been formed. This is termed an "etch back" procedure.

A second method accesses the release layer from the edge of the wafer or sample only and releases the material as one large sheet. This second method is for cases which do not require registration between devices lifted from the same wafer. If registration is not desired, an automated procedure is used for liftoff of large areas of individual devices or areas of material. After frontside processing is completed, UV cured epoxy can be cured with the desired pattern, removed where it is not wanted, and then used as the mask for etching down to the release layer. The UV cured epoxy can then be left on and can act as support for the lifted films after separation. The separate devices would then need to be retrieved from the etching solution and processed separately using pick and place type methods.

These alternative lift-off processes will now be described in connection with FIGS. 10A–10E, wherein corresponding items in FIG. 9 retain the same reference numeral if FIG. 10. As shown in the partial perspective cross-section of FIG. 10A, a substrate 202 has formed thereon a release layer 204, followed by a device structure 206, all as described in connection with FIG. 9. All front side processing, such as bonding pads and metal contacts (not shown) to the structure 206 are completed.

A material which can be transformed from a less soluble or less etchable state to a more soluble or more etchable state (or vice versa) is formed on the front-side processed structure 206. For example, a UV curable epoxy 230 can be spread over the structure 206. This epoxy has the property that exposure to UV light causes it to be less soluble.

A UV light transparent mask release layer 232 of material is then formed over the epoxy 230 and a patterned opaque mask 234 with openings 236 is affixed over the layer 232.

The mask 234 is irradiated with UV light, curing the areas of the epoxy underlying the mask openings 236 and making them less soluble than in the uncured state. The release layer 232 is removed by and the mask 234 is removed. Next, the uncured epoxy is removed by a solvent, such as down to the release layer 204 (See FIG. 10B).

The cured epoxy 230 is left on the structure to serve as a support for the thin film structure 206 after separation from the release layer 204. In this manner, the etching front is increased by dividing up the total top surface area of structure 206 into smaller areas by cutting channels 240 down to the release area 204.

A second method for wafer size liftoff relies on increasing the amount of etching front by dividing up the total area to be lifted into smaller areas. Channels are cut into the total area of material to be lifted thereby exposing the release layer. These channels can completely separate the area or can consist of slits cutting part way into the liftoff area.

Figure 10A:
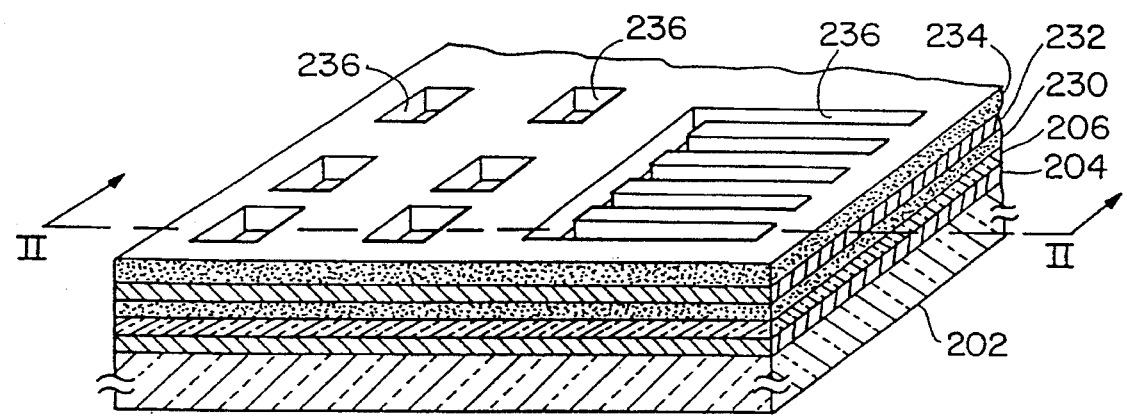
FIG. 10A is a partial perspective view of a wafer during lift-off processing according to another embodiment of the invention.
Figure 10B:
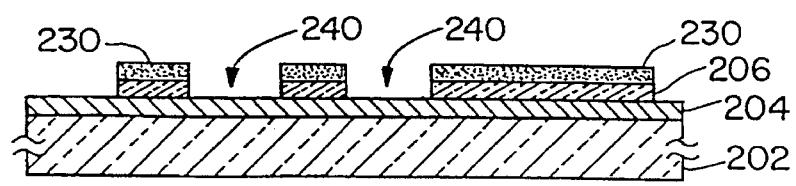
FIG. 10B is a sectional view taken along lines II—II of FIG. 10A of the lift-off structure after a step in the process.
Figure 10C:
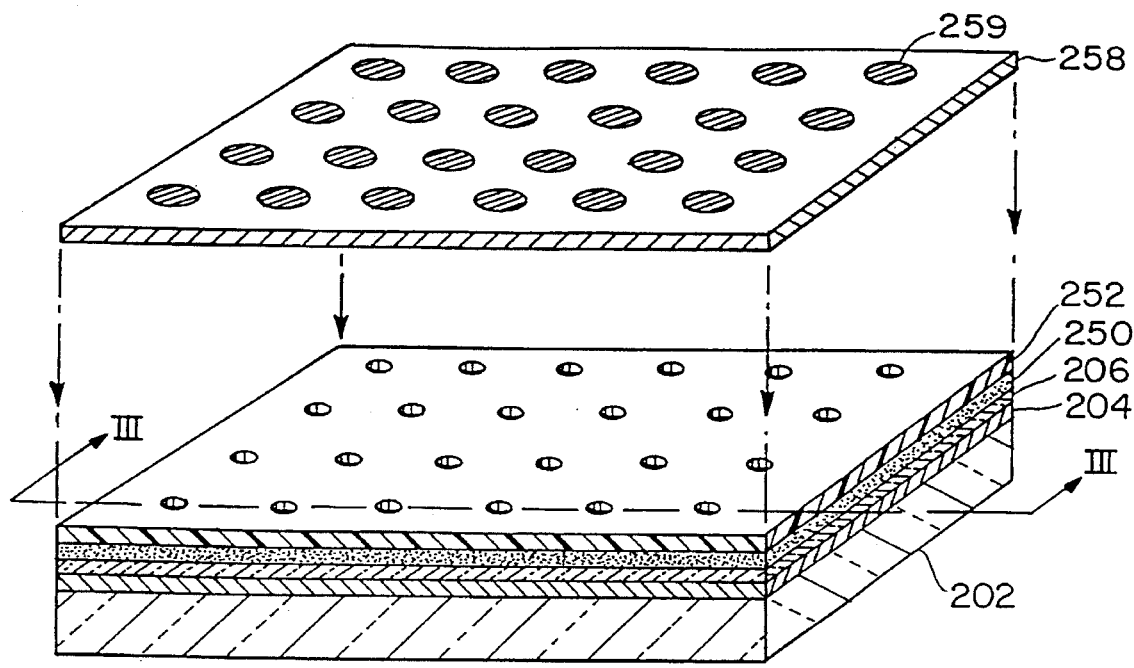
FIG. 10C is a partial perspective view of a portion of a wafer during lift-off processing in another embodiment where registration is maintained.
Figure 10D:
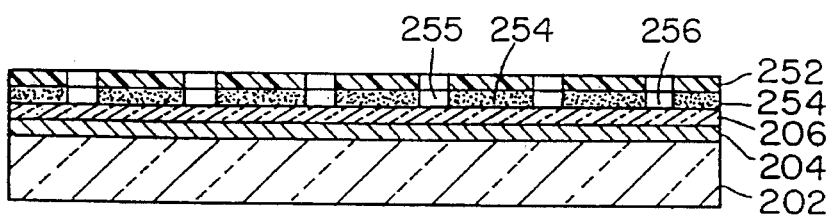
FIGS. 10D and 10E show cross-sections of the structure of FIG. 10C after additional steps in the lift-off process.
Figure 10E:
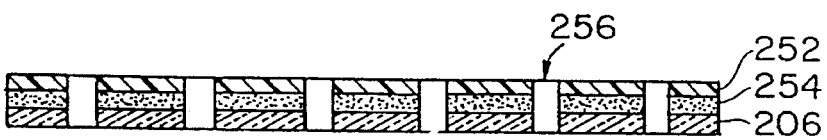

The second method addresses the problem of trying to register these small areas of material with respect to each other while at the same time allowing the etching medium greater access to the exposed release layer. The ability to do this allows for easy retrieval from the solution, wafer scale processing on the backside, and short liftoff times due to the smaller areas and maximum exposure of the etching front. The key feature of this approach is that it allows for registration of the entire wafer area while still providing the etching solution access to all the etching fronts.

Where registration between devices is required, as in an array of transistors, the lift-off method of the alternate embodiment of FIGS. 10C–10E offers many advantages.

This alternate process of FIG. 10C solves the difficult problem of trying to register small device or pixel areas of material with respect to each other, while at the same time, allowing the etching medium access to the exposed release layer. The ability to do this allows for easy retrieval from the solution, wafer scale processing on the backside, and short lift-off times due to the smaller areas and maximum etching front. This approach also enables registration of devices throughout the entire wafer area while still providing the etching solution access to all the etching fronts. Turning to FIG. 10C, there is shown a rectangular partial section of a wafer. The wafer is formed of a semiconductor substrate 202 upon which a release layer 204 is deposited by CVD followed by a front processed transistor panel 206, all as previously described above.

Transformable material, such as uncured liquid UV epoxy 250 is spread onto the top or front surface of structure 206. The point of departure with the previous embodiment occurs in the next step, when a perforated planar grid 252, made of transparent material, such as plastic, is aligned on top of the epoxy 250. The perforations 256 extend orthogonal to, and through, the plane of grid 252.

A photo-mask with opaque circles 256 aligned to cover the perforations 256 is then affixed over the grid 252 (FIG. 10C). (An optional UV transparent mask release layer (not shown) may be formed between the mask 258 and grid 252 to facilitate mask removal.) UV light is focused onto the mask, curing the underlying epoxy 254 everywhere except beneath the opaque circles 254, as shown in FIG. 10D wherein the cured sections of epoxy 250 are shown in shaded section and the uncured sections are in blank. The mask 258 is removed. The uncured epoxy 250 is removed from the openings 256 by a suitable solvent and structure 206 etched away through the openings down the the release layer 204. The release layer is then etched away using the opening 256, as provided above. Access for the etchant is thus achieved at many points across the wafer, resulting in an array being attached to grid 252 by cured epoxy 254 (See FIG. 10E).

Figure 11A:
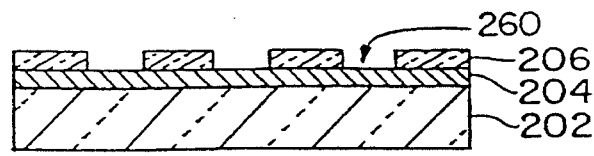
FIGS. 11A–11E are schematic drawings of a wafer during various steps in the process flow of a lift-off procedure in accordance with the invention.
Figure 11B:
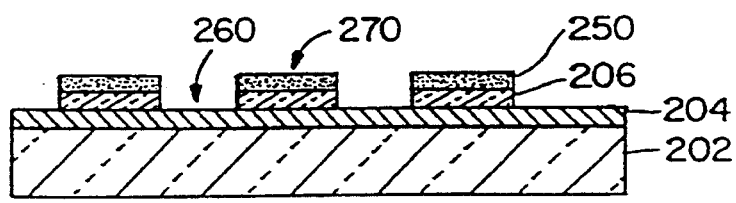
Figure 11C:
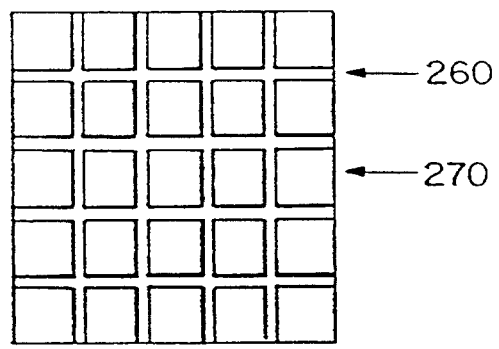
Figure 11D:
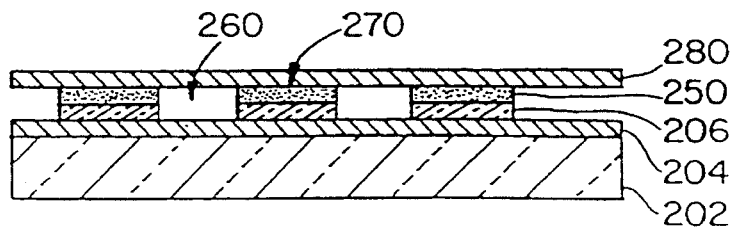
Figure 11E:
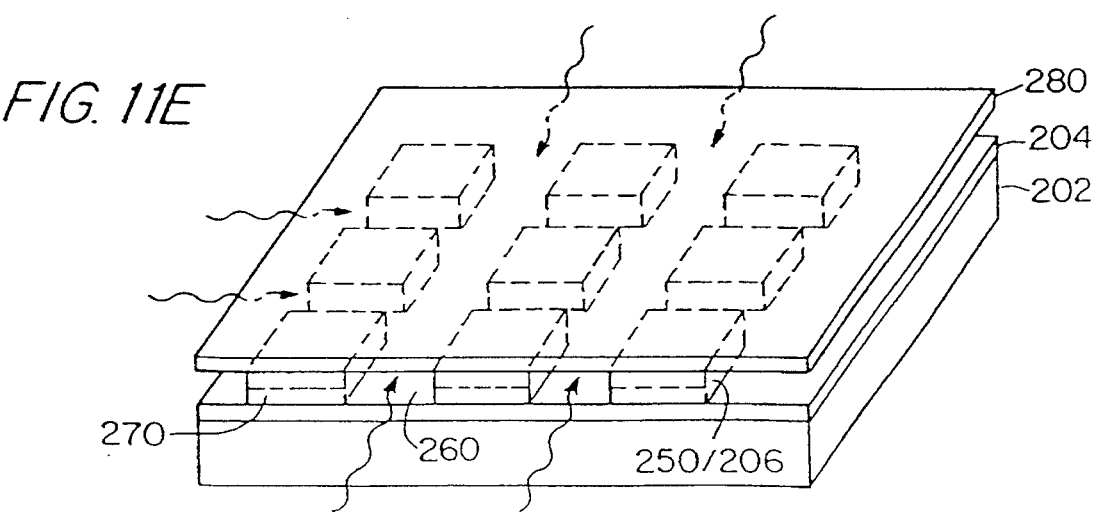

Another approach to registration is to form channels 260 directly in the device material by etching down to the release layer 204, thereby forming channels in the material alone (FIG. 11A). These channels can also be made taller by using the UV cured epoxy patterning method of FIG. 9 and then etching down to the release layer 204, (See FIG. 11B), or any other method that forms channels 260 or access streets between the areas 270 to be separated, as shown in the plan view of FIG. 11C. A support 280 can then be attached to the material 270 over the channels 260 and then the etchant can be allowed to run along the channels, thereby giving the etchant access to the center of the wafers (FIGS. 11D–11E). Taller channels can assist in speeding up the capillary action to achieve faster release. Other methods can also be used to speed along the movement of the etchant up the channels 260, including vacuum assistance, ultrasonic assistance, etc.

Along the same lines, channels 260 can be made in the device material to expose the release layer below. A porous material is then spun on, or otherwise formed or attached to the front surface. This material is rigid or semi-rigid when cured by UV, heat, or solvent treatment, etc., and therefore able to support the lifted film after separation from the substrate. The material is sufficiently porous to pass the etchant fluid without being attacked by the etchant. In this way, the etchant passes through the porous material and is given access to the release layer at its exposed points.

In another embodiment, the release layer etchant is brought in contact with the release layer before the overlying support structure is attached to the structure 206. For this process to work, channels 260 must be formed between devices or areas of material to be lifted for the etchant to be trapped in. The basic process is as follows: Channels 260 are formed between lift-off areas 206 which expose the release layer 204 on substrate 202. This can be done with any of the previously described methods which create channels between devices. A simple method which works very well is to form the channels directly in the material 206 by photoresist masking followed by etching down to the release layer 204. This forms channels 260 in the material which are equal to the height of the material above the release layer. Next, an etchant is placed on the surface of the layer to be lifted, or the wafer is submerged in the etchant. In either case, the channels 260 between the areas to be lifted 206 are filled with the etchant material. After this is done, the overlying support layer, which will also hold the registration after lift-off, is affixed to the front surface of the structure 206 by bonding methods described in detail herein. The overlying support is secured to the material 206 while the wafer is submerged or while the etchant is covering the front surface of the wafer and filling the channels. The support materials must be rigid enough that they do not fill in the channels that have been formed and thereby force the etchant out. A suitable support material can comprise glass, plastic or other optically transmitting substrate. This allows for a solid support medium that does not need etchant access holes in it, thus greatly simplifying the process.

The trapped etchant sufficiently dissolves the release layer 204 so that the thin film area 206 can be removed while being supported and registered by support with the backside exposed for further processing, i.e., formation of backside conductor metallization and bonding pads.

In addition to the support materials referenced above, UV release tapes, which are well known in the industry for handling small devices, have proven to be an excellent support choice for several reasons. These tapes have the property that when exposed to intense UV radiation, they lose most of their adhesion. In addition, moisture does not seem to effect the adhesive, and they can be applied with great success, even if submerged in liquid. These tapes can be used alone or in conjunction with a thicker support. This additional support should be formed of material which is transparent to UV radiation unless it is to be permanent and it should not be attacked by the etchant being used.

Figure 12A:
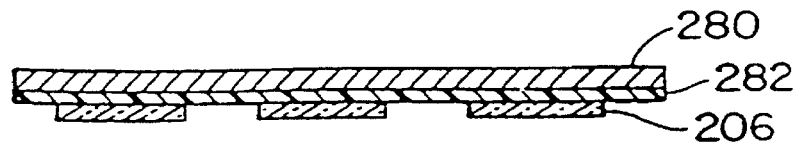
FIGS. 12A–12C are schematic sectional drawings of another preferred lift-off procedure of the invention.
Figure 12B:
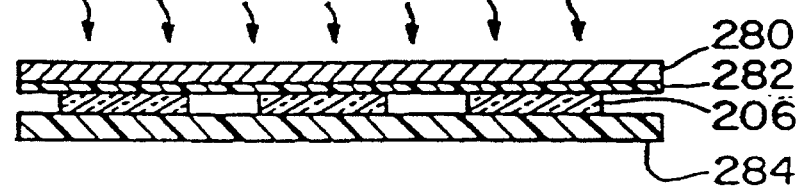
Figure 12C:
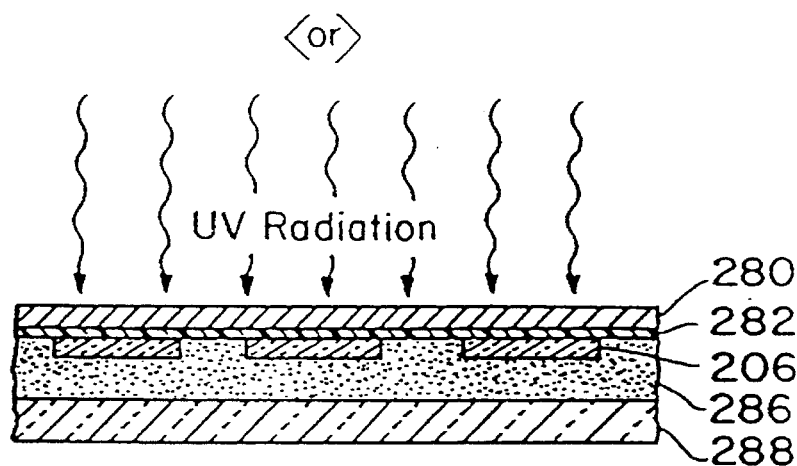

The UV release adhesive can be applied directly to other support materials, instead of the tape backing material. As shown in FIGS. 12A–12C, support 280, combined with double-sided UV release tape 282, can be used. One side of the tape 282 is adhered to the support. Then the other side is adhered to the front of the structure 206 after the etchant is applied. The etchant is then allowed to undercut the device 206. The devices are then attached by release tape to the support 280, as shown in FIG. 12A. The lift-off time is very short because the etchant has access to the release layer from many points on the wafer surface.

In this way, the devices are registered with respect to each other and are supported by the support 280 during backside processing.

The tape's adhesion can then be released by UV irradiation through the support (FIGS. 12B or 12C) and the tape can be taken off the carrier 280 with the devices still attached. Further UV exposure will decrease the adhesion of the devices to the tape to a sufficient degree to allow the devices to be removed by vacuum wand or to be transferred directly from the tape to any other tape 284 or epoxy 286 with substrate 288 (See FIGS. 12B or 12C) or other medium. Separate areas as large as 0.5 cm in width have been lifted by this non-curvature method. Total wafer size, which can be lifted and registered simultaneously, is only limited by the wafer size.

As indicated, an alternative embodiment involves use of UV-cured adhesive tapes and epoxies. The adhesive can be used to bond the thin-film transistors and CMOS circuit elements to glass. The adhesive is applied to plates that are as large, or larger than, 14"×14". Application methods include: spin coating, vapor coating, spraying, and standard thick film application processes to provide the necessary uniformity and optical quality.

Another preferred embodiment includes a method to transfer tightly placed devices to positions not so tightly spaced on the circuit panel. The technique illustrated in FIGS. 13A, B and C uses stretching or contracting of a stretchable tape or film until the devices are positioned correctly. This technique can also include previously described lift-off procedures and mechanical or a combination of stretching and mechanical methods. Commercially available devices can be used to precisely control the stretching of the film. Various methods can be used to measure the spacing of devices during stretching and transfer to provide proper registration of components.

As illustrated in FIG. 13A in connection with structure 300, an array of transistors or thin-film semiconductor regions 304 has been transferred onto a stretchable substrate 302. Transistors or regions 304 have been fabricated and transferred in accordance with the procedures set forth above, or using any other suitable procedure. Substrate 302 can comprise an adhesive.

In a first embodiment the structure is stretched along axis 306, as shown in FIG. 13B, thereby increasing the distance 308 between devices 304 along axis 306 while leaving the distance 310 between devices in another direction the same. The substrate 302 is then stretched along axis 314 to produce the array shown in FIG. 13C where devices 04 have spacing 308 in one direction and spacing 12 in an orthogonal direction.

In another embodiment the structures 300 of FIG. 13A is stretched simultaneously in directions 306 and 314 to provide the array shown in FIG. 13C.

Figure 14A:
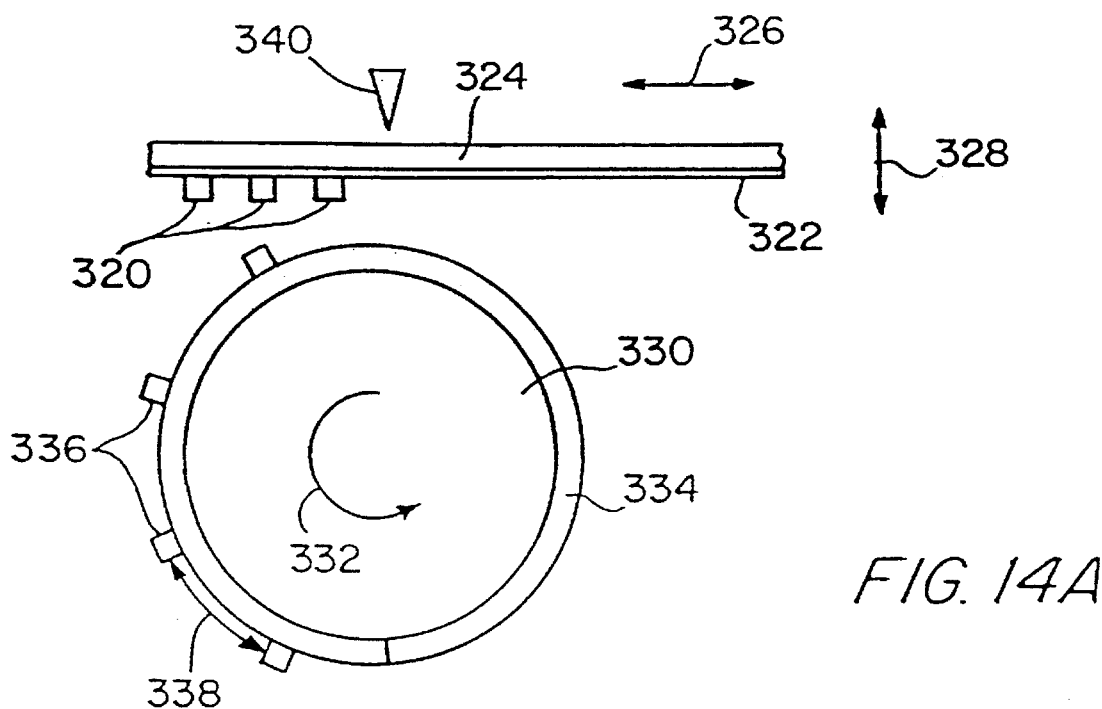
FIGS. 14A and 14B schematically illustrate additional transfer methods in accordance with the invention.
Figure 14B:
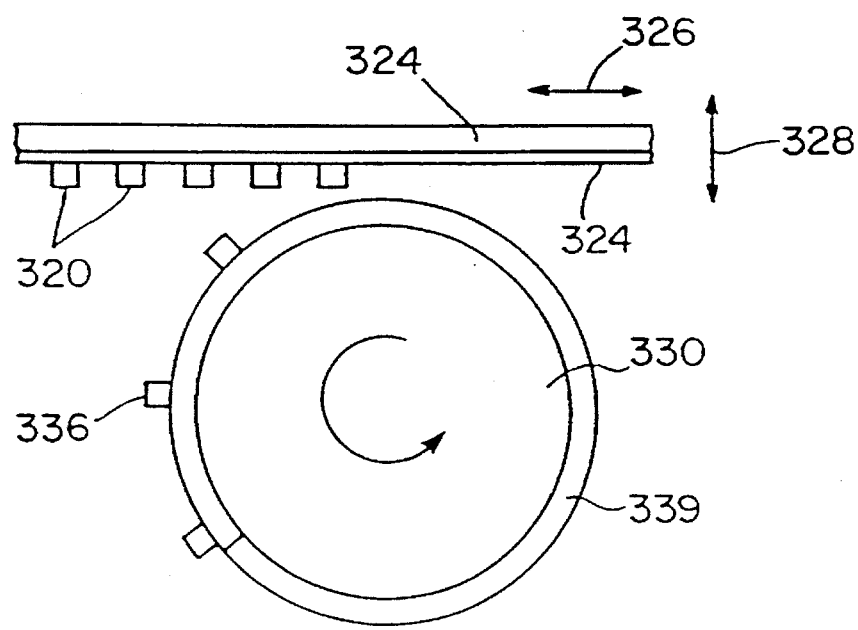

A mechanical technique is shown in FIGS. 14A and B. One starts with a lifted off array of devices 320 on a tape. This tape 322 is placed on a frame 324 that moves in and out along axis 326 and up and down along axis 328. A drum 330 with a flexible tape 334 is placed around its circumference. A instrument 340 is then pushed onto the device 324, pushing the first row of devices onto the drum tape 334. The drum tape 334 is indexed in direction 332 at the necessary angle and again the instrument 340 pushes a second row of devices with spacing 338 onto the tape 334. This continues until all the rows are transferred. This first drum tape 334 with the rows of devices 336 is then put onto frame 324. The same operation continues by transferring rows onto a new drum tape 339.

Another embodiment is to stretch the tape in one direction, transfer this to another tape and stretch that tape in the other direction and transfer the devices to the final support. This method is well suited for small disconnected devices.

Figure 15:
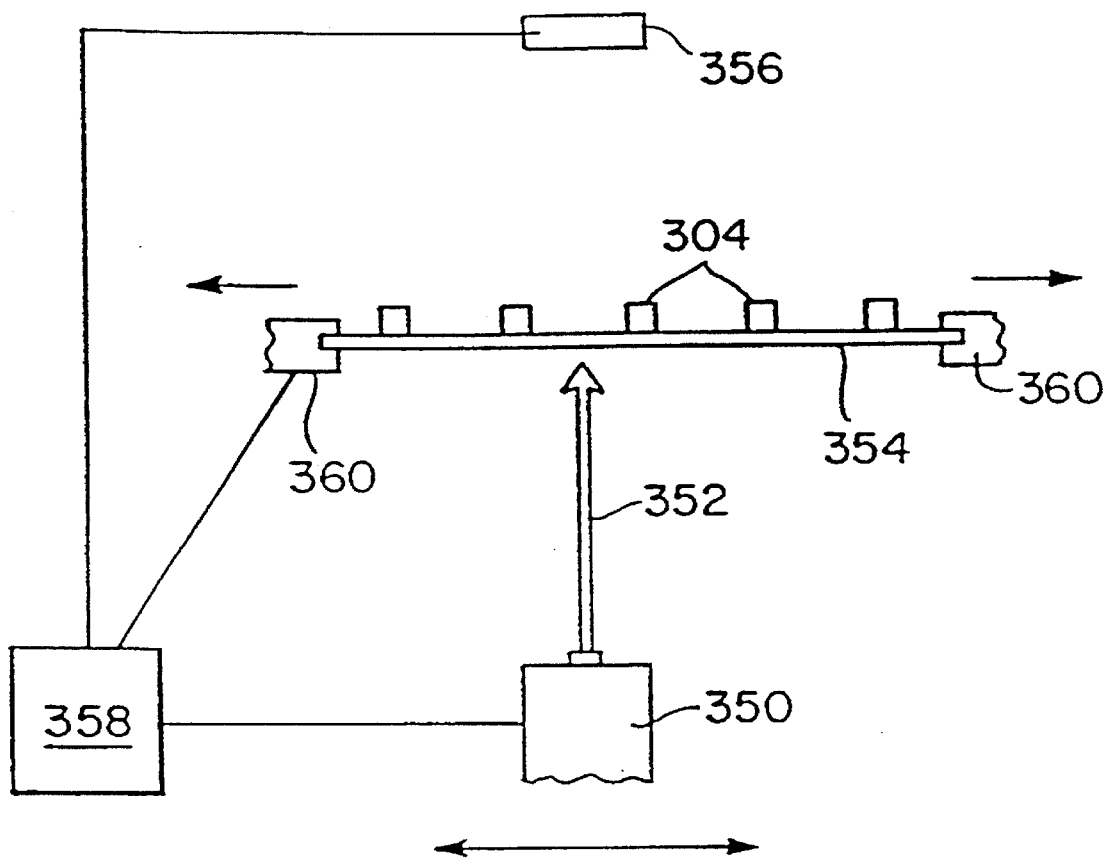
FIG. 15 illustrates a preferred system for monitoring and controlling device registration in accordance with the invention.

A system for measuring the distance between devices 304 on a transfer or final substrate is shown schematically in FIG. 15. A laser 350 directs a beam 352 in the direction of substrate 354 and scans across the source. Sensors 356 are positioned to detect transmitted and/or reflected light an generate signals where the beam is deflected by a device 304. A controller 358 correlates movement of the beam 352 relative to the substrate 354 so that the distance between the devices 304 is accurately measured. Controller 358 is electrically connected to stretching mechanism 360 so that adjustments can be made to the spacing of selected rows or columns of devices.

Stretching mechanism 360 can consist of a piston that is pressed through a collar to which the substrate 354 is attached. The movement of the piston face against substrate 354 and through the collar stretches substrate 354 in a precisely defined manner to increase the spacing between devices 304.

Alternatively, there are commercially available stretching mechanisms like that shown in FIG. 15 which grip the substrate along its periphery and precisely pull the substrate in the appropriate direction.

After stretching the registered devices are transferred to glass, polyester or other suitable substrate for light valve (LCD) fabrication. Alternatively, the devices can be mounted onto light emitting devices for display fabrication.

We claim:

1. An active matrix display comprising:

an optically transmissive substrate;

a silicon-on-insulator structure bonded to the optically transmissive substrate with an adhesive layer, the silicon-on-insulator structure having an array of transistor circuits formed therewith in a first plane to provide an active matrix array such that each transistor circuit is connected to a pixel electrode in an array of pixel electrodes;

a counterelectrode panel extending in a second plane that is parallel to the first plane such that the insulator extends between the first plane with the array of transistors and the second plane; and a light transmitting material positioned over each pixel electrode such that actuation of a transistor circuit in the array alters an optical transmission property of the light transmitting material over the pixel electrode connected to the actuated transistor circuit.

2. The active matrix display of claim 1 wherein the light transmitting material comprises an electroluminescent material.

3. The active matrix display of claim 1 wherein the light transmitting material comprises a liquid crystal material.

4. The active matrix display of claim 1 wherein the silicon-on-insulator structure comprises a layer of single crystal silicon over an insulating layer.

5. The active matrix display of claim 1 further comprising an array of color filter elements positioned over the array of pixel electrodes.

6. The active matrix display of claim 1 further comprising first and second driver circuits formed with the silicon-on-insulator structure.

7. An active matrix display comprising:

an optically transmissive substrate;

a silicon-on-insulator structure bonded to the optically transmissive substrate with an adhesive layer, the silicon-on-insulator structure having an array of transistor circuits formed therewith to provide an active matrix array such that each transistor circuit is connected to a pixel electrode in an array of pixel electrodes; and a liquid crystal material positioned over each pixel electrode, the insulator extending between the liquid crystal material and the array of transistor circuits such that actuation of a transistor circuit in the array will alter an optical transmission property of the material over the pixel electrode connected to the actuated transistor circuit.

8. The active matrix display of claim 7 wherein the insulator is positioned between the array of transistor circuits and the liquid crystal material.

9. The active matrix display of claim 7 wherein the adhesive comprises a transparent polymeric epoxy.

10. The active matrix display of claim 7 wherein the silicon-on-insulator structure comprises a layer of single crystal silicon over an insulating layer.

11. The active matrix display of claim 7 further comprising an array of color filter elements positioned over the array of pixel electrodes.

12. The active matrix display of claim 7 further comprising first and second driver circuits formed with the silicon-on-insulator structure.

13. The active matrix display of claim 7 wherein the silicon-on-insulator structure comprises a silicon film in which a majority of crystals extend over a cross-sectional area, in a plane extending laterally through the silicon film, of at least $0.1$ cm$^2$.

14. An active matrix display comprising:

an optically transmissive substrate;

a silicon-on-insulator structure bonded to the optically transmissive substrate with an adhesive layer, the silicon-on-insulator structure having an array of transistor circuits formed therewith to provide an active matrix array such that each transistor circuit is connected to a pixel electrode in an array of pixel electrodes;

a light transmitting material positioned over each pixel electrode, the insulator extending between the light transmitting material and the array of transistor circuits such that actuation of a transistor circuit in the array of transistor circuits will alter an optical transmission property of the material over the pixel electrode connected to the actuated transistor circuit; and a color filter array positioned over the pixel electrodes.

15. The active matrix display of claim 14 wherein the light transmitting material comprises an electroluminescent material.

16. The active matrix display of claim 14 wherein the light transmitting material comprises a liquid crystal material.

17. The active matrix display of claim 14 wherein the silicon-on-insulator structure comprises a layer of single crystal silicon over an insulating layer.

18. The active matrix display of claim 14 wherein the adhesive comprises a transparent polymeric epoxy.

19. The active matrix display of claim 14 further comprising first and second driver circuits formed with the silicon-on-insulator structure.

20. The active matrix display of claim 14 wherein the silicon-on-insulator structure comprises a silicon film in which a majority of crystals extend over a cross-sectional area, in a plane extending laterally through the silicon film, of at least $0.1$ cm$^2$.

\* \* \* \* \*

UNITED STATES PATENT AND TRADEMARK OFFICE
CERTIFICATE OF CORRECTION

PATENT NO. : 5,528,397
DATED : June 18, 1996
INVENTOR(S) : Paul M. Zavracky et al.

It is certified that error appears in the above-identified patent and that said Letters Patent is hereby corrected as shown below:

Column 1,
Line 12, prior to "BACKGROUND OF THE INVENTION", insert the following:
-- GOVERNMENT SUPPORT
The invention was supported, in whole or in part, by grants N00014-90-C-0045, N00014-90-C-0050, N00014-93-C-0187, and N00014-94-C-0250 from the United States Navy. The Government has certain rights in the invention. --.

Signed and Sealed this

Thirteenth Day of December, 2005

JON W. DUDAS
*Director of the United States Patent and Trademark Office*